US011450224B1

(12) United States Patent
Jain et al.

(10) Patent No.: US 11,450,224 B1
(45) Date of Patent: *Sep. 20, 2022

(54) CUSTOMIZING HEALTH PROGRAMS BASED ON INDIVIDUAL OUTCOMES

(71) Applicant: Vignet Incorporated, Fairfax, VA (US)

(72) Inventors: Praduman Jain, Fairfax, VA (US); Dave Klein, Oakton, VA (US); Yue Cao, Vienna, VA (US); Neeta Jain, Fairfax, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/082,482

(22) Filed: Oct. 28, 2020

Related U.S. Application Data

(63) Continuation of application No. 16/783,273, filed on Feb. 6, 2020, now Pat. No. 11,127,308, which is a
(Continued)

(51) Int. Cl.
*G09B 7/02* (2006.01)
*G06F 3/14* (2006.01)
(Continued)

(52) U.S. Cl.
CPC ............... *G09B 7/02* (2013.01); *G06F 3/14* (2013.01); *G06F 8/61* (2013.01); *G06F 8/65* (2013.01);
(Continued)

(58) Field of Classification Search
CPC .... G09B 7/02; G09B 5/06; G06F 3/14; G06F 8/61; G06F 9/453; G06F 8/65;
(Continued)

(56) References Cited

U.S. PATENT DOCUMENTS 7,447,643 B1   11/2008 Olson et al.
9,361,011 B1    6/2016 Burns
(Continued)

FOREIGN PATENT DOCUMENTS

AU       2014213012       1/2014

OTHER PUBLICATIONS

Khanacademy.org, [online] "Khan Academy," Available on or before Nov. 2, 2012, via Internet Way back Machine URL <http://web.archive.org/web/20111202083549/http://www.khanacademy.org/> retrieved Apr. 11, 2019, 19 pages.

*Primary Examiner* — Pei Yong Weng
(74) *Attorney, Agent, or Firm* — Fish & Richardson P.C.

(57) ABSTRACT

In some implementations, one or more computers provide data for an application configured to provide interactive content personalized for a user of a mobile device. The one or more computers obtain activity data for the user for a current segment of the program. The activity data can include interaction data indicating one or more interactions of the user with the application during the current segment and sensor data indicating one or more measurements separate from user input to the application. The one or more computers identify a subset of content for the current segment based data indicating on a current track or level assigned for the user. The one or more computers cause a selected portion of the content in the subset to be presented on the mobile device in response to a determination, based at least in part on the sensor data for the current segment, that one or more triggers or conditions defined by rules associated with the current track or level are satisfied.

20 Claims, 11 Drawing Sheets

Related U.S. Application Data continuation of application No. 15/694,372, filed on Sep. 1, 2017, now Pat. No. 10,565,892, which is a continuation of application No. 15/152,411, filed on May 11, 2016, now Pat. No. 9,753,618.

(51) Int. Cl.

| | | |
|---|---|---|
| *G09B 5/06* | (2006.01) | |
| *G06F 8/61* | (2018.01) | |
| *G16H 20/70* | (2018.01) | |
| *G06F 9/451* | (2018.01) | |
| *G06F 8/65* | (2018.01) | |
| *G16H 20/30* | (2018.01) | |

(52) U.S. Cl.
CPC ............... *G06F 9/453* (2018.02); *G09B 5/06* (2013.01); *G16H 20/30* (2018.01); *G16H 20/70* (2018.01); *G06F 3/1454* (2013.01); *G09G 2354/00* (2013.01)

(58) Field of Classification Search
CPC ......... G06F 3/1454; G06F 8/20; G16H 20/30; G16H 20/70; G09G 2354/00
See application file for complete search history.

(56) References Cited

U.S. PATENT DOCUMENTS

| | | |
|---|---|---|
| 9,426,433 B1 | 8/2016 | Mazzarella |
| 9,753,618 B1 | 9/2017 | Jain |
| 2004/0203755 A1 | 10/2004 | Brunet et al. |
| 2005/0186550 A1 | 8/2005 | Gillani |
| 2005/0246304 A1 | 11/2005 | Knight et al. |
| 2006/0041452 A1 | 2/2006 | Kukarni |
| 2006/0205564 A1 | 9/2006 | Peterson |
| 2007/0281285 A1 | 12/2007 | Jayaweera |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0311968 A1 | 12/2008 | Hunter |
| 2009/0023555 A1 | 1/2009 | Raymond |
| 2009/0172002 A1 | 7/2009 | Bathiche |
| 2010/0082367 A1 | 4/2010 | Hains et al. |
| 2010/0211941 A1 | 8/2010 | Roseborough |
| 2010/0250341 A1 | 9/2010 | Hauser |
| 2011/0184748 A1 | 7/2011 | Fierro et al. |
| 2011/0200979 A1 | 8/2011 | Benson |
| 2013/0110565 A1 | 5/2013 | Means |
| 2013/0179472 A1 | 7/2013 | Junqua |
| 2014/0088995 A1 | 3/2014 | Damani |
| 2014/0156823 A1 | 6/2014 | Liu |
| 2014/0186810 A1* | 7/2014 | Falash ............ G09B 5/06 434/308 |
| 2014/0240122 A1 | 8/2014 | Roberts |
| 2014/0273913 A1 | 9/2014 | Michel |
| 2015/0019342 A1 | 1/2015 | Gupta |
| 2015/0056589 A1 | 2/2015 | Zhang et al. |
| 2016/0021040 A1 | 1/2016 | Frei |
| 2016/0058287 A1 | 3/2016 | Dyell |
| 2017/0286605 A1 | 10/2017 | Wong et al. |
| 2018/0341378 A1 | 11/2018 | Morrow |
| 2020/0175886 A1 | 6/2020 | Jain et al. |

* cited by examiner

| RULE | TRIGGER(S) | CONDITION(S) | ACTION |
|---|---|---|---|
| PROGRAM RULE 1 | PROGRAM MODULE A: WHEN A USER REACHES PERSONAL WEEKLY ACTIVE MINIMUM GOAL | PERIOD = 1<br>TRACK = DOG WALKING<br>LEVEL = MODERATE | - DELIVER VIDEO 1 FOLLOWED BY ASSESSMENT 1 TO USER DEVICE<br>- DELIVER EMAIL 1 TO EMAIL ADDRESS |
| PROGRAM RULE 2 | PROGRAM MODULE A: WHEN A USER REACHES PERSONAL WEEKLY ACTIVE MINIMUM GOAL | PERIOD = 1<br>TRACK = DOG WALKING<br>LEVEL = VIGOROUS | - DELIVER VIDEO 2 FOLLOWED BY ASSESSMENT 2 TO USER DEVICE<br>- DELIVER EMAIL 2 TO EMAIL ADDRESS |
| PROGRAM RULE 3 | PROGRAM MODULE A: WHEN A USER REACHES PERSONAL WEEKLY ACTIVE MINIMUM GOAL | PERIOD = 2<br>TRACK = DOG WALKING<br>PREVIOUS LEVEL = MODERATE<br>LEVEL = MODERATE | DELIVER RANDOM CONTENT ITEM FROM CATEGORY A OF CONTENT LIST |
| PROGRAM RULE 4 | PROGRAM MODULE A: WHEN A USER REACHES PERSONAL WEEKLY ACTIVE MINIMUM GOAL | PERIOD = 2<br>TRACK = DOG WALKING<br>PREVIOUS LEVEL = VIGOROUS<br>LEVEL = MODERATE | DELIVER RANDOM CONTENT ITEM FROM CATEGORY B OF CONTENT LIST |

FIG. 4

CUSTOMIZING HEALTH PROGRAMS BASED ON INDIVIDUAL OUTCOMES

CROSS-REFERENCE TO RELATED APPLICATION

This application is a continuation (and claims the benefit of priority under 35 USC 120) of U.S. application Ser. No. 16/783,273, filed Feb. 6, 2020, now U.S. Pat. No. 11,127, 308, which is a continuation of U.S. application Ser. No. 15/694,372, filed Sep. 1, 2017, now U.S. Pat. No. 10,565, 892, which is a continuation of U.S. application Ser. No. 15/152,411, filed May 11, 2016, now U.S. Pat. No. 9,753, 618. Each of the prior applications is incorporated by reference in its entirety.

GOVERNMENT LICENSE RIGHTS

This invention was made with government support under grant number HHSN261201500013C awarded by the National Institutes of Health. The government has certain rights in the invention.

FIELD

This specification generally describes technology related to dynamically generating application data.

BACKGROUND

Applications for computers, mobile devices, and other devices can provide useful functionality to users. Users generally install and run many different applications, each with a different purpose and set of functionality. Frequently, applications are coded and maintained separately, at considerable effort and cost. Applications are often individually stored and distributed through application store or marketplace, requiring significant server resources for distribution and storage. Further, user devices have limited storage space. This limited space is often taken by applications that are each useful for only limited functions, or by applications that each only partially serve the user's needs.

Many applications operate using a series of fixed user interfaces or dialogs that may not be appropriate for all users. For example, many applications provide the same general layout and type of content for novice users and expert users, without tailoring the content to the user's specific needs. As another example, in the area of healthcare management, applications are generally not able to customize their user interfaces and content to address users' diverse range of medical conditions, unique rates of progress, and varying preferences.

SUMMARY

In some implementations, an application architecture uses a server system that interacts with client devices to dynamically provide personalized content in mobile applications. The server system can store and update program data that defines multiple different programs that are each available to users through the same single application. The program data can divide each program into a sequence of multiple segments corresponding to different time periods. The program data can also define different tracks that represent different types of content or functionality within the program, as well as different levels within each track. These tracks and levels can span many or all of the segments, allowing a user to transition between different experiences while maintaining a consistent progression through the segments of the program over time.

In some instances, mobile applications can be used to deliver healthcare content to electronic devices of users. However, some applications can be under-inclusive because they are designed to target a specific patient population affected by a complex medical condition that is not prevalent among the general population. For example, an application focused on the needs of patients receiving chemotherapy is generally inapplicable to users who are not affected by cancer. Other applications can be over-inclusive because they are designed to target a large population but fail to adequately provide a personalized experience for an individual user. For example, mobile applications that target a broad user audience by providing general services often fail to provide the necessary personalized experience to keep users engaged and meet their specific needs. As a result, many health-related mobile applications are often unable to be used to treat a variety of disease conditions while also being relevant to a broad spectrum of patient populations.

To address these concerns, programs can designed with modular features to provide individual users within a general population with different groups of content that are each personalized for the specific needs of the individual users. For instance, such modularized features can include different time period segments within a single program, and different groups (or arrangements) of content to be provided for each time period. In this regard, the overall program can be applicable for the general population whereas individual modules can be used to segment specific user groups and provide personalized groups using the modular features. In some implementations, a system stores program data for a program that provides interactive content over a series of multiple time periods. In some instances, the transitions between the multiple time periods can be used to represent different milestones associated with an individual user's progress through the program. In other instances, the transitions can simply represent the passage of time since a user has enrolled into a program. Each time period also includes a set of user-selectable tracks that provide different categories of personalized content to analyze the progress of the individual user through the program. For example, a performance level for the user can be measured based on the individual user's activity within each track.

As the user progresses through the different time periods of the program, the system can periodically adjust the content displayed on a mobile device associated with the individual user based on the user's activity within the different tracks. For instance, the system uses a set of rules that specify the content to be displayed on the mobile device based on satisfying corresponding conditions and triggers. This content can be of a variety of types, including, for example, notifications, media (e.g., images, animations, videos, audio, text), interactive elements including surveys and assessments, and so on. The triggers and conditions can be specified for the different time periods, tracks and performance levels such that the content provided to the program is adaptive to the user's ongoing activity throughout the program.

The system enables an administrator such as a healthcare provider or insurer to monitor the ongoing activity of the individual user and adjust the triggers and conditions of the set of rules to provide content that is directed to increasing the likelihood that the individual user will complete the program. In this regard, the system can be used as a content delivery platform to a variety of users using different programs that supply different content and user experiences, and also personalize each program for each individual user.

In some implementations, a computer-implemented method includes: storing, by the server system, program data for a program that provides interactive content to an application that runs on mobile computing devices, the program comprising a sequence of multiple segments each corresponding to different time periods, the program comprising multiple selectable tracks and multiple levels within each track, the program data indicating rules for the program that vary the interactive content provided to different users according to at least the respective tracks, levels, and segments of the program associated with the different users; receiving, by the server system, activity data from a mobile computing device indicating interaction of a particular user with the mobile computing device during a particular segment of the multiple segments of the program; accessing, by the server system, data indicating that the particular user is associated with the program, and data indicating a current segment, a current track, and a current level for the particular user in the program; identifying, by the server system and from among the rules indicated by the program data, a rule that corresponds to the current segment, the current track, and the current level in the program for the particular user; determining, by the server system, that a trigger of the identified rule is satisfied and that one or more conditions specified by the identified rule are satisfied; and in response to determining that the trigger of the identified rule is satisfied and that the one or more conditions specified by the identified rule are satisfied, providing, by the server system, content specified by the identified rule for display in the application of the mobile computing device associated with the particular user.

Other versions of these and other aspects disclosed herein include corresponding devices, systems, and computer programs encoded on computer-readable storage devices that are configured to perform the actions of the methods. These and other aspects may include one or more of the features discussed below.

In some implementations, providing the content specified by the identified rule for display at the client device associated with the particular user includes providing access to a new track not included among the multiple selectable tracks within the program data of the program of the particular user.

In some implementations, providing the content specified by the identified rule for display at the client device associated with the particular user includes providing an interactive assessment that is selected based at least on the accessed data indicating the current segment, the current track, and the current level for the particular user in the program.

In some implementations, determining that the trigger of the identified rule is satisfied includes determining that the accessed data indicates that the particular user transitioned from a previous segment of the program to the current segment of the program within a particular range of time.

In some implementations, providing the content specified by the identified rule for display at the client device associated with the particular user includes: in response to determining that the accessed data indicates that the particular user has been associated with the current segment, selecting, by the server system, one or more user-selectable tracks from among the multiple selectable tracks within the program data that are associated with the current segment; and providing data identifying the selected one or more user-selectable tracks for display at the client device associated with the particular other user.

In some implementations, determining that the one or more conditions of the identified rule is satisfied includes determining that the current level for a particular track is greater than a predetermined threshold level specified by the identified rule.

In some implementations, providing the content specified by the identified rule for display at the client device associated with the particular user includes: in response to determining that the current level for a particular track is greater than a predetermined threshold level for the particular track specified by the identified rule, selecting a plurality of tracks from among the multiple selectable tracks within the stored program data that are determined to be similar to the current track; and providing the selected one or more tracks for display at the client device associated with the particular other user.

In some implementations, the identified rule that corresponds to the current segment, the current track, and the current level in the program for the particular user includes an arrangement specification for the content specified by the identified rule for display at the client device associated with the particular user.

In some implementations, the method further includes: adjusting the arrangement of the content specified by the identified rule for display at the client device associated with the particular user based at least on arrangement specification of the identified rule.

In some implementations, the method further includes: in response to determining that the trigger of the identified rule is satisfied and that the one or more conditions specified by the identified rule are satisfied, generating, by the one or more computers, an instruction for the application of the mobile computing device associated with the particular user indicating a new time period in the program for the particular user; and providing the instruction indicating the new time period in the program for the particular user to the client device associated with the particular user.

In some implementations, the server system performs operations including: providing, to a third party system, an interface for an administrator of the third party system; receiving, from the third party system and through the interface, program data that alters the rules for the program that vary the interactive content provided to different users according to at least the respective tracks, levels, and segments of the program associated with the different users; and applying the altered rules for the program to adjust interaction of the application of the mobile computing device with the particular user.

In some implementations, the data identifying the selected one or more user-selectable tracks for display at the client device associated with the particular other user includes: a data package including content for the current segment, the current track, and the current level in the program for the particular user; an instruction for the mobile computing device associated with the particular user to clear a program data cache of the application of the mobile computing device; and a set of rules corresponding to the current segment, the current track, and the current level in the program for the particular user, the set of rules specifying adjustment techniques used by the application of the mobile computing device to customize the content for the current segment, the current track, and the current level in the program for the particular user.

In some implementations, the rules for the program include one or more global rules and one or more rules that apply to each program.

In some implementations, the activity data received from the mobile computing device includes data collected by one or more sensors that exchange communications with the mobile computing device.

The details of one or more implementations are set forth in the accompanying drawings and the description below. Other potential features and advantages will become apparent from the description, the drawings, and the claims.

BRIEF DESCRIPTION OF THE DRAWINGS

FIG. 4 is a diagram that illustrates examples of rules that can be used to adjust content associated with a program.

In the drawings, like reference numbers represent corresponding parts throughout.

DETAILED DESCRIPTION

Figure 1A:
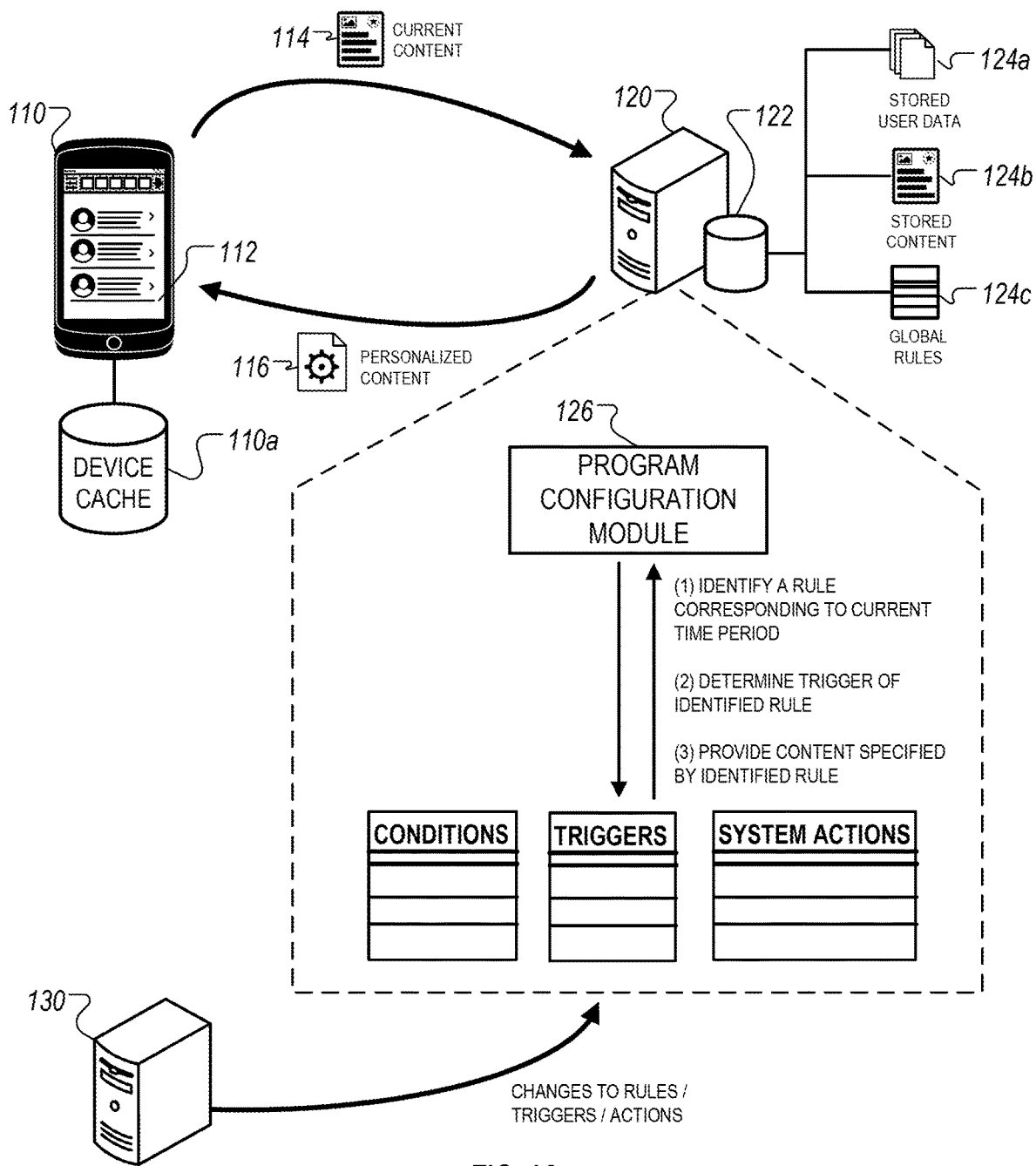
FIGS. 1A-1C are diagrams that illustrate examples of a content distribution system.

In general, a system stores program data for a program that provides interactive content over a series of multiple time periods. The transitions between the multiple time periods can be used to represent different milestones associated with an individual user's progress through the program. Each time period also includes a set of user-selectable tracks that provide different categories of personalized content to analyze the progress of the individual user through the program. For example, a performance level for the user can be measured based on the individual user's activity within each track.

As the user progresses through the program sequence of the program, the system uses a set of rules with triggers and conditions associated with the time period, track, and performance level to dynamically provide content within the program. For instance, the triggers of the rules can be used to detect when the user transitions between time periods or when changes in the user's performance level with respect to particular tracks take place, and the conditions of the rules can be used to determine when the user's progress and/or performance level satisfies the requirements to transition between different periods of the program sequence.

The technical architecture of the system further provides various improvements in administering personalized content to individual users, which often require significant storage resources on client devices. In some implementations, the technical architecture of the system enables a client device to provide administering personalized content to individual users without using significant storage with the use of a dynamic application cache. For instance, techniques for data processing and analysis associated with the program can be performed by a remote server so that the client device automatically receives personalized content for the individual user instead of having to store different content items that are manually requested by user over time. For example, instead of the client device requesting content from the remote server, the server can automatically determine the content to provide to the mobile application as discussed herein. In this regard, the remote server can periodically transmit data packages including content items to be provided to the individual user, instructions to install and display the content included in the transmitted data packages, or instructions to caching or removing old content items that are no longer relevant to the program from the storage of the client device, instructions to reconfigure the display of the interface on the mobile application. This periodic data exchange between the remote server and the client device enables the client device to utilize fewer computational resources such as memory or storage in operating the mobile application to provide the individual user with a personalized experience. In some instances, the remote server may receive data from a third party system that adjusts the operations performed by the remote server.

To minimize the computational resources requirements necessary to provide personalized content, the system utilizes a set of global rules that enable a server to perform a smaller number of processing steps to provide personalized experience for all users while providing varied user interfaces. For instance, the rules can be used to adjust types of content provided for each individual user using a set of common adjustment and distribution schemes to allow for use shared resources in providing personalized content for groups of users that are predetermined to be similar to one another. For example, the server may be capable of clustering content data based on prior activity within a program, similar demographic information, by similar programs, among other types of classifications.

The set of global rules can vary in scope and in hierarchy to enable the system to select particular rules from the set of global rules to adjustably execute aspects associated with the data processing of the personalized content. In this regard, the system may select applicable rules to guide data processing in order to maximize resource allocation efficiency. For example, rule selection may be based on the different types of content to be provided, the size of the content to be provided, and/or the number of users that are associated with particular types of content to be provided.

As described herein, a "program" refers to a set of rules or instructions that define a user experience provided through an application. As discussed below, a program can include collections of interactive content and rules that define when and how content should be delivered through an application. Although a program can include executable software, it is not required to be defined in this manner. Rules that define a program may be interpreted by multiple devices, including user device and server systems, to create the customized user experiences that a program provides. In some implementations, at least part of a program is implemented as a service, with one or more server systems dynamically selecting and delivering at least some of the program content to a client device, customized for a specific user.

As discussed further below, a program can be structured with a variety of divisions. For example, programs can be defined to include a sequence of segments, where each segment lasts for a fixed or variable time period. Users who begin a program progress consistently through a segment as time passes, and then progress from one segment of the program to the next. For example, a program defined to last for a year could be divided into 52 week-long segments or 12 one-month segments. Each segment may involve the different user experiences, content, and rules. In some implementations, a user moves from one segment to the next purely by passage of time, while in other implementations, a user may be required to satisfy additional criteria to progress to the next segment. In addition to the segments, programs can also be divided into different tracks and different levels, discussed further below.

The program can indicate specific features of an application that an organization selects to provide to the user. When downloaded and stored on a user device, program data may configure an associated mobile application to provide custom content and interactions for a particular user. When the user subsequently runs the application, the application retains the configuration, appearance, and interactivity specified by the previously downloaded program data. The mobile application can provide a user with a customized user experience of a native mobile application without the need for the client organization to code and register an application with an app store (e.g., the Apple App Store, or Google Play for Android Apps, etc.). For wellness-related programs, the program enables the user and the organization that provides the program to perform specific types of data tracking and reporting according to a user's specific medical needs, or the priorities of the client organization (e.g., to encourage and reward exercise, or to promote quitting smoking, etc.). In this regard, the program can be customized to the goals of the user.

Programs can be created and administered for a wide variety of topics and purposes. Some examples below describe ways that a program may be used to encourage and assist a user to improve health, e.g., by establishing better habits or helping to deal with a medical condition. The techniques of generating, delivering, and using programs is not limited to healthcare, however, and the same techniques can be used to provide customized user experiences to many other types of applications.

A "program sequence" refers to a set of user milestones that are used to indicate a user's progress within the program. The program sequence generally includes a set of time-variable periods that can represent different iterative stages within the program sequence. For example, a program sequence may specify psychological user conditions that are commonly associated with a particular treatment program, physical conditions associated with a post-operative recovery period, or a set of intermediate requirements that a user must satisfy to advance through the program. The program sequence can also be used to customize the arrangement of content to be provided on the program for each user. For example, survey data obtained from the user can be used to adjust the program sequence of each program such that the progress milestones are designed around a user's specific medical history, demographic information, among other types of information.

A "period" refers to a defined time segment that indicates a user's progress within a program. For instance, multiple periods of different specified time lengths can be sequentially arranged to represent different clinical treatment stages associated with a medical condition of the program. The period can be used to specify a progress measure indicating a user's performance within the program. The progress measure can be calculated based on, for example, amount of time spent on specific content provided on the program, overall amount of time spent within the program, or amount of time spent by the user compared to an expected level of time for based on data obtained from similar users within the same program. The period can also be used to adjust content to be provided to a user. For example, the program can be configured such that targeted content for a specific period is provided on the program once the progress measure indicates that the user has transitioned into a particular period. Likewise, content previously displayed on the program can also be removed once a user transitions to a new period where the previously displayed content is determined to be no longer relevant.

A "track" refers to user-selectable collections of content to be provided on the program. In some implementations, the tracks are alternatives, and only one track is active at a time. In other implementations, a user may be able to have multiple tracks of a program active simultaneously. Different tracks can represent different topics or categories of content that can be provided to a user based on, for example, the current period the user is in within the program, medical conditions or procedures associated with the user, or demographic information associated with the user. In this regard, the arrangement of content tracks within a program can be used to customize the program for each individual user by providing a user with access to certain tracks that are predetermined to the relevant to the user. In some instances, particular tracks may be designated as period-specific such that these tracks are only provided to the user when the user is in a particular period of the program. In other instances, tracks may be grouped together by similarities in content provided on the program.

A "level" refers to a determination of a user's performance within a particular track. For instance, a single track may include various levels that are each associated with a set of user performance requirements. A user may be designated to a particular level based on the types of user input provided on the program. For example, a track associated with exercise may have different levels that each correspond to different levels of user fitness. In this example, measured sensor data provided by the user can be used to estimate a user fitness and designate a corresponding level for the user's performance within the exercise track. Level designations for the user can also be used to adjust the display of content on the program. For instance, a particular track may have prerequisites such as a minimum level within an associated track, and once the user is designated to the minimum level, the particular track may be provided for display on the program.

An "arrangement specification" refers to the collection of tracks that are provided for selection by a user. For instance, the arrangement specification can be specified based on a particular period such that each period within the program sequence includes a different arrangement specification to assist with the user's progress through the various periods of the program. In other instances, the arrangement specification can be specified on the attributes of an individual user (e.g., age, gender, location, etc.) such that the arrangement specification can be used to personalized a collection of tracks that are provided to each individual user.

A "performance level measure" refers to a designation of a user's current level within a particular track. The performance level measure can be used as an indicator of the user's performance within the particular track. For example, a high performance level measure can indicate that the user has been designated to higher levels of difficulty within the particular track, which can then be used to infer that the user has achieved a minimum level of proficiency to successfully satisfy the requirements associated with the particular track. In addition, individual performance level measures for each tracks can be aggregated to compute a user's overall performance within a particular period. For example, if a particular period provides a user with three tracks, then the performance level measures for each of the three tracks can be aggregated to represent the user's overall performance within the particular period.

A "progress measure" refers to a user's current status within the program, which can be used to indicate the user's overall performance within the program. In some instances, the progress measure can be an aggregated score of the individual performance level measures for each track as described above. In other instances, the progress measure may be further augmented with additional metrics such as a time spent within a particular period relative to the overall time spent within the entire program, a comparison of the time spent within the current period and the time spent within the previous period, among others. The progress measure can also be used to determine when a user should be transitioned to a subsequent period within the program sequence of the program.

An "administrator" refers to an entity or individual that interacts with an administrator portal of the content distribution system to designate specific tracks to provide to a user on program. In some instances, the administrator is an employee or representative of the client organization that manages and updates the customized module. For instance, the administrator can use an administrator portal of the publishing system to select from various options and provide specifications for a desired module. Additionally, the administrator may identify a list of users that are eligible to receive the module, data indicating applicable healthcare providers or insurance plans, access privileges associated with particular features of the health management modules, or custom content for health management modules.

A "healthcare provider" refers to individuals, institutions, or organizations that provide healthcare services to users. In some instances, the healthcare provider can be an individual health professional such as a physician, or an entity such as a hospital that provides preventative, curative, or rehabilitative programs for users, or a health insurance provider. Healthcare providers can use a provider portal to interact with the publishing system, both to submit information that is accessed through appropriate modules and to receive information from users of certain modules to use in enhancing treatment. As an example, healthcare providers may submit health-related information such as electronic health records, treatment program information, or promotional material. This information may be general for a group of users (e.g., for all users who have a particular insurance plan) or specific to individual users. In some instances, the information submitted on the provider portal can be compiled into a set of module information that is used to personalize the display and operation of the customized health management modules to the provider.

A "user" or "patient" refers to an individual that uses a mobile application and one or more customized modules. In some instances, the user receives healthcare-related services from the healthcare provider. For instance, the user can use a mobile application that is customized using a healthcare module created on behalf of the user's employer, the user's insurance company, or another entity.

Figure 1B:
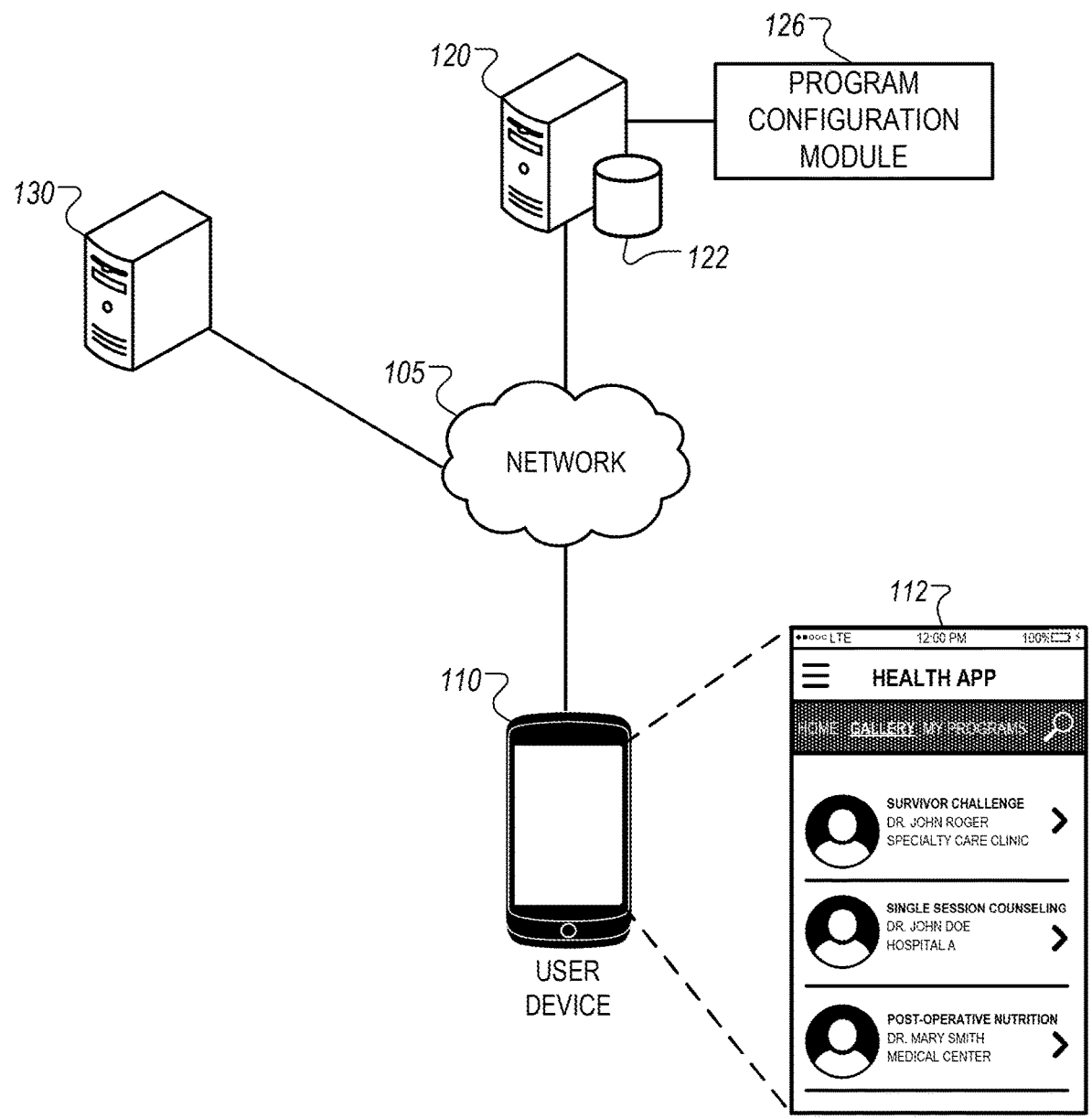
Figure 1C:
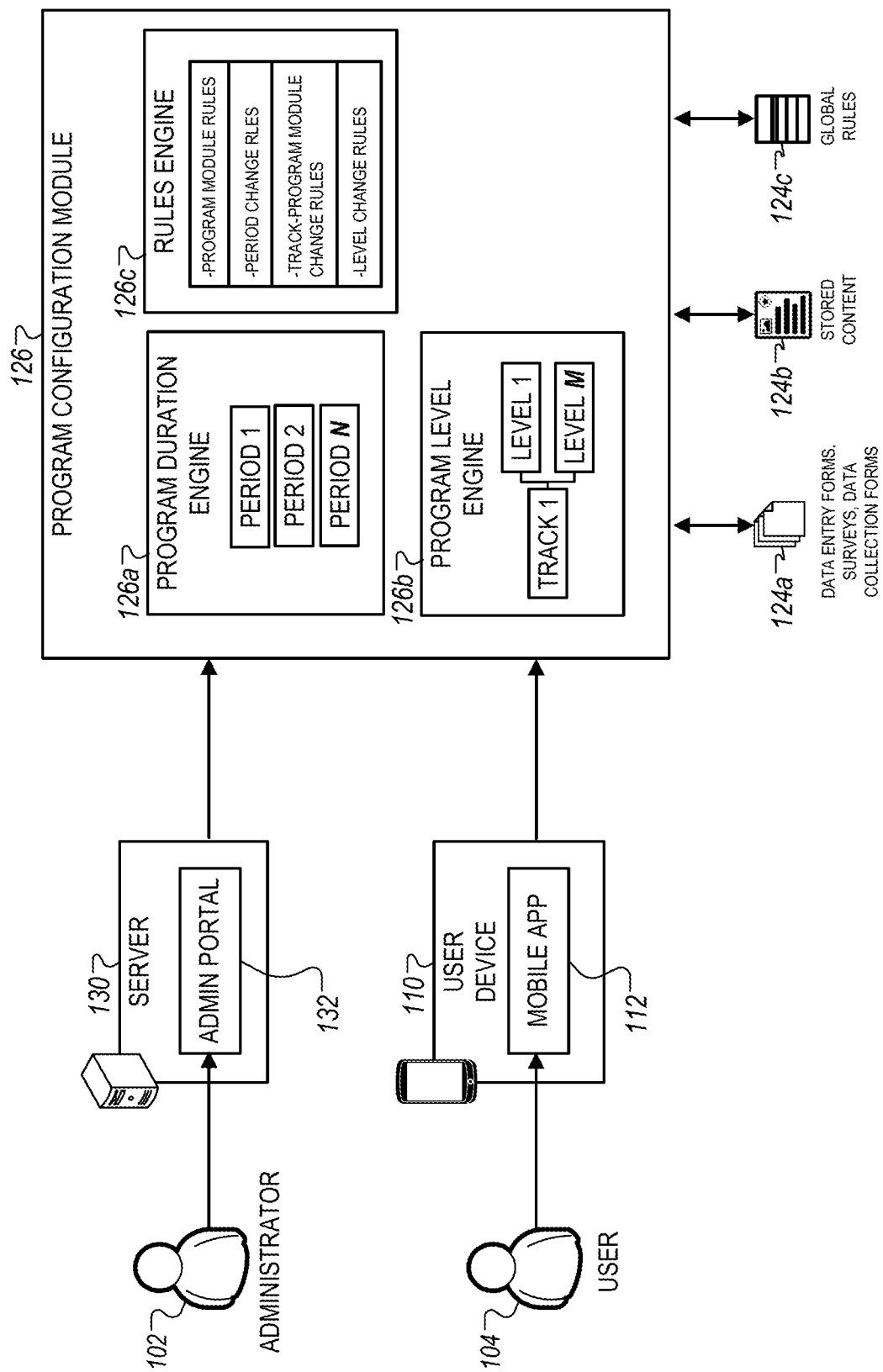

FIGS. 1A-1C are diagrams that illustrate examples of a content distribution system 100. FIG. 1A illustrates a diagram of an example of personalized content generation processes performed by the system 100. FIG. 1B illustrates a block diagram of the system 100, which generally includes a user device 110, and servers 120, 130 connected over a network 105. The server 120 includes a program configuration module 126, which generates and adjusts configuration and generation of content to be provided on a mobile application 112 on the user device 110. FIG. 1C illustrates a diagram of the program configuration module 126 in greater detail.

In general, the technical architecture of the system 100 enables the server 120 to perform resource-intensive data processes such that the resources necessary to operate the mobile application 112 on the user device 110 to provide a personalized user experience is minimal. For example, the server 120 periodically exchanges communications with the user device 110 such that updated content is automatically transmitted to the user device 110 without a manual request from content being transmitted by the user (e.g., an update). The periodic exchange between the server 120 and the user device 110 also enables automatic updating of content to be provided on the mobile application 112 without requiring the client device 110 to download and store additional content while also storing prior content in storage. For example, in each data communication with the client device 110, the server 120 transmits a set of instructions that cause the client device 110 to delete content items that is no longer determined to be relevant or useful to the progress of the user through the software program, and instead install additional content items that are to be provided for display on the mobile application 112. In this regard, the periodic exchange between the user device 110 and the server 120 enables the client device 110 to utilize less storage to execute the mobile application 112 to provide the user with a personalized experience.

Referring to FIG. 1A, the user device 110 and the server 120 may periodically exchange communications to update content provided to a user on the mobile application 112. In general, the user device 110 initially transmits current content 114 to the server 120. The server 120 then performs a set of operations based on program data stored on a database 122 of the server 120, e.g., stored user data 124a, stored content 124b, global rules 124c, and then determines personalized content 116 to be provided to the mobile application 112 based on a set of program rules, conditions and triggers.

In more detail, current content 114 may be data generated by the mobile application 112 indicating a current time period, a current track, and a current level for the user associated with the user device 110. For instance, for a particular program within the mobile application 112, the current content 114 may specify a list of tracks that are presently available to the user, and for each track, user performance level data indicating a current level, and a user progress measure indicating a current time period within the particular program. In some instances where a user participates in multiple programs within a certain time period, the current content 114 also includes data for each of the multiple programs.

The current content 114 can include user input data including, for example, survey response data submitted by the user on the mobile application 112 while interacting with user-selectable content associated with a particular track, user selections in response to requests for information provided within a track, among other types of user input data. The current content 114 can also include sensor data received by the user device 110 and provided by the user while participating in activities associated a particular track. For example, sensor data can include heart rate measurements of a user during an exercise-related activity, a picture of the user and/or a region of the body of the user undergoing treatment, or physiological measurements made by external devices that exchange data communications with the user device 110 during a specified period of a particular program.

The current content 114 is received by the server 120, which then compares the data included within the current content 114 to program data stored in the database 122. The program data can include stored user data 124a, stored content 124b, and global rules 124c. The user data 124a represents historical and demographic information associated with the user. For example, the user data 124a can include registration information that is submitted by the user after initially installing the mobile application 112 and/or enrolling in a particular program. Such information can include identifying information (e.g., name, age, sex, and social security number) as well as medical history, and ongoing medical conditions (e.g., current prescriptions, treatment schedules, and recent operations).

The stored content 124b can include prior data received by the server 120 during an earlier transmission from the user device 110. For example, the user data 124a can include data indicating prior programs that the user participated in, and for each prior program, the prior tracks accessed by the user. The stored content 124b can also include statistical information associated with the prior user activity data. For example, the statistical information for a particular program can include percentage of tracks successfully completed, average time period for track completion, number of level advancements for various tracks, average performance level measures for a particular time period, among others. In each of these examples, the stored content 124b may include data that is reflective of user activity within a particular program, a particular period within a particular program, and/or for a particular track within the particular time period. In this regard, the accumulated data within the stored content 124b can be used to derive data trends that can be analyzed to prepare automated recommendations to either provide to the user in subsequent programs, or to generate custom content to be provided to a user during subsequent programs.

The global rules 124c can be a set of configuration rules associated with protocols for various programs that are provided on the mobile application 112. The global rules 124c can be used to trigger the display of specific user-selectable content based on the data in the current content 114 satisfying one or more rules conditions specified by the global rules 124c. An example of a global rule can be providing access to new tracks based on determining, based on the current content 114, that the user has advanced to a new time period within the program sequence of a particular program. Another example of global rule can be providing a notification on the user on the mobile application 112 based on determining that the user has advanced to a new level within the track.

In general, the rules of a program can have an assigned scope of applicability. Different rules may be designated to apply for only specific segments, tracks, or levels within a program. Rules may be defined for combinations of these program elements. For example, a rule may be defined to apply only during a particular segment or time period of a program and also only for a particular track and level within the track. The data for each rule may include a value or code that indicates its applicability, allowing the appropriate rules for any given portion of a program to be efficiently identified. In some implementations, the rules are arranged in a hierarchy, with some rules being applicable to a program in its entirety, some rules being applicable only for specific time periods, and others being applicable in more specific situations. Also, the computer systems that allow administrative users to build programs can provide user interfaces that allow the administrative users to alter a program by adjusting the applicability of the rules, to efficiently adjust the user experiences provided by the program.

The stored server 120 includes a program configuration module 126 that compares the received current content 114 and compares the data included within the current content 114 to the stored data within the database 122 to perform a variety of tasks that are described more particularly below. However, for simplicity, FIG. 1A depicts an example of an operation where the program configuration module 126 generates personalized content 116 based on comparing the data included within the current content 114 against a set of program rules, conditions, and triggers associated with a particular program.

In the example depicted in FIG. 1A, the program configuration module 112 identifies a rule corresponding to a current time period within the current content 114, determines an applicable trigger of the identified rule, and provides custom content 116 from the database 122 that is specified by the identified rule. A greater description of the program rules, conditions, and triggers are provided with respect to FIG. 3.

The program rules, conditions, and triggers used by the program configuration module 126 may be adjusted over time based on ongoing user activity on the mobile application 112 such that, as a user progresses through multiple periods within a program, the program configuration module 126 is capable of dynamically adjusting the techniques used to generate the personalized content 116. In this regard, as the user progresses through a particular program, feedback provided on the mobile application 112 can be augmented and adjusted by the program configuration module 126 based on adjustments made to the program rules, conditions, and triggers associated with the particular program. More particular descriptions of such adjustments are provided with respect to FIG. 1C.

The personalized content 116 provided to user device 112 can include adjustments to programs provided on the mobile application 112. The adjustments can include providing additional content to be displayed on the program, providing access to content that was previously displayed but inaccessible to the user, and/or removing content that is no longer determined to be relevant or necessary to the user's progress through the program. For example, where program configuration module 126 determines that the current content 114 indicates that a user has satisfied the requirements for a particular period, the personalized content 116 may include data for a subsequent period within the program. In another example, where the program configuration module 126 determines a user's performance level measure within a particular track has substantially increased, data for additional tracks within a particular time period can be included to provide the user with different tracks to advance through the particular time period. Other examples of the personalized content 116 are provided in the descriptions below.

In some implementations, the personalized content 116 includes instructions from the server 120 adjust a device cache 110a associated with the mobile application 112 on the client device 110. The device cache 110a may store data associated with the mobile application 112 (e.g., application configuration data, computer-implemented instructions to operate the mobile application 112) or program data associated with a user associated the client device 110. For example, the device cache 110a can include user data from prior tracks, content previously transmitted from the server 120, among other types of data used by the mobile application 112. In such implementations, the instructions included in the personalized content 116 may specify instructions to add or remove content from the device cache. For example, the instructions can specify removal of data associated with a prior track or period of the program to reduce the storage space on the user device 110 necessary to execute the personalized content 116. As another example, the user device 110 can determine which cached data no longer corresponds to the current period, level, or track of the user in the program, and may delete the unneeded content as a result.

The caching of data at the user device 110 allows shared processing of program rules by the user device 110 and the server 120. The data cached at the user device 110 can include subsets of program rules dynamically selected by the server 120, in some instances, a customized subset of rules selected for a particular user. For example, the server 120 may determine the current period, track, and level of a user in a specific program, and send a data package that includes only the rules that define behavior affecting the user for that portion of the program. The server 120 may further filter the rules according to the characteristics of the user (e.g., the user's personalized goals or history of use of the program) exclude rules that are not applicable, to limit the amount of data transferred to and stored at the user device 110. The user device 110 receives the data package including the rules, stores it, and processes the subset of rules locally, allowing for quick response times for user interaction and continuation of the program when the user device 110 may not have a network connection to communicate with the server 120.

In some implementations, the operations performed by the program configuration module 126 may be updated and/or changed based on a set of instructions received from the server 130. For instance, the changes can include alterations to the conditions, triggers, and/or system actions used to determine the content to include within the personalized content 116, addition of new rules that impact the selection of content to be provided within the personalized content 116, among other types of adjustments. In some instances, the server 130 can be monitored and operated a third party organization (e.g., a healthcare provider, a health insurer) that is separate from the organization that operates the server 120.

FIG. 1B is a block diagram that illustrates an example of the system 100 for distributing custom content for a program. As depicted, the user device 110, the server 120, and the administrator system 130 can be connected over a network 105. The server 120 additionally includes the program reconfiguration module 126 for generating personalized content 116 based on receiving data transmissions from the administrator system 130 and the user device 110. The personalized content 116 is then transmitted over the network 105 for display on a user interface of the mobile application 112.

The server 120 can periodically exchange data with the user device 110 over the network 105. For example, the server 120 can receive user input data and user behavior data associated with a user's participation in a program from the user device 110. The program configuration module 126 can be a module of the server 120 that processes the received data transmissions from the device 110 and the server 130 and determines the personalized content 116 to be provided on the mobile program 112a. For example, as described more particularly with respect to FIG. 3, the program configuration module 126 may determine whether one or more conditions associated with a rule indicated by program stored on the server 120 are satisfied.

In some implementations, the program configuration module 126 can be a component that is executed on the user device 110. The program configuration module 126 may be configured to operate based on a set of computer-implemented instructions stored locally on the user device 110. Other arrangements can also be possible. For example, the functions of the program configuration module 126 may be split between the server 120 and the user device 110. In another example, the server 120 may periodically provide updates to rules and other program data stored on the user device 110, and application the user device 110 may apply the rules and provide the personalized content 116.

The user device 110 can be any of various types of electronic devices that are capable of providing a user interface. Although FIGS. 1A-1C depict the user device 110 as a smartphone, in some implementations, the device 110 can be a tablet computing device, a laptop computing device, a desktop computing device, or a wearable device (e.g., a smart watch, glasses, or a bracelet). In addition, the user interface provided on the user device 110 may include information provided through a visual display, but may additionally or alternatively provide information through, for example, audio output, haptic output, and electroshock, which may be dynamically configured based on information associated with the user.

The personalized content 116 to be provided on the mobile application 112 may be based on various user actions on the user interface of the mobile application 112. For example, depending on a user's responses to visual notifications, audible notifications, electroshock stimulations and haptic notifications such as vibrations of the user device 110. For example, if notifications requiring user action are dismissed, the performance level metric of the user can be reduced to indicate inactivity, which is then used to provide personalized content 116 that is more interactive for the user. In addition, the personalized content 116 may adjust the appearance of visual notifications, as well as the sound, volume, or length for audio notifications, and the intensity, pattern, or type of haptic outputs.

In some implementations, the system 100 includes one or more other servers 130 or other devices that provide information that is used to reconfigure the program. For example, a mobile application may communicate with independent, third-party systems operated by a user's healthcare provider, health insurance provider, or employer. The mobile application 112 may display additional user-selectable content on the program in response to receiving information from these third-party systems. Similarly, information from these third-party systems may be used to select which content should be presented and determine how prominently the content should be displayed (e.g., at what size or ranking in a list the content should be shown). For example, the mobile application 112 may access electronic medical records (EMR) from a user's physician to determine or verify a user's care plan, and then configure the program to include information corresponding to that care plan. As a result, mobile application 112 can be automatically updated to provide, for example, physician appointment reminders, medication reminders, encouragement for health plan compliance, instruction and information, and surveys related to the care plan. Similarly, when an employer's health plan options and incentives change, the server 110 can be notified and the interface reconfiguration module 126 can reconfigure the interface to inform the user.

FIG. 1C is a diagram that illustrates the types of data transmissions received and processed by the program reconfiguration module 126 to generate personalized content 116.

Briefly, an administrator 102 and a patient (e.g., user) 104 may provide input on the admin portal 132 and the mobile application 112, respectively, which is then transmitted to program reconfiguration module 126 by the server 130 and the user device 110. As described previously with respect to FIG. 1B, the server 130 can be associated with one or more organizations that either administer or monitor a user's progress on a program (e.g., a primary healthcare provider or a health insurance company), or an entity that generates, maintains, or provides content to be access by the user (e.g., a healthcare content provider or a specialty treatment clinic). In addition to the data received from the server 130 and the user device 110, the program configuration module 126 can also receive data stored on the server 120, for example, stored user data 124a, stored content 124b, and global rules 124c as described previously with respect to FIG. 1A.

The program configuration module 126 includes a set of sub-modules for determining whether conditions and/or triggers associated with the program are satisfied based on the data received from the server 130 and the user device 110 and the program data stored on the database 122. For instance, the program configuration module 126 includes a program duration engine that computes a user progress measure, a program level engine 126b that computes a user performance level measure, and a rules engine 126c that compares the information included in the received data to determine if the triggers and/or conditions associated with a set of program-specific rules have been satisfied.

The program duration engine 126a enables the program configuration module 126 to track the overall progress of the user 104 through the program sequence of the program. For example, the program duration engine 126a is capable of extracting data from the current content 114 as depicted in FIG. 1A and identify the current time period of the user 104. The program duration engine 126a also compares the current time period of the user 104 and the prior time periods indicated within the stored content 124b to determine the progress of the user 104 between the present condition and the last received content from the user device 110.

In one example, the program duration engine 126a computes a progress measure for a particular period based on a set of requirements associated with the period. The value of the progress measure is then used to represent a user's progress through the particular period. In this example, the value of the progress measure can be compared between successive data transmissions from the user device 110 to measure a user's development through the period. In another example, the program duration engine 122 performs a set of tests to detect when the user 104 has transitioned between successive periods. In this example, the program duration engine 126a can aggregate the values for a set of performance level measurements for each of the multiple tracks within a particular period, and determine that the user has satisfied the requirements for the particular period based on determining that the aggregate performance level measurement exceeds a threshold value. In yet another example, the program duration engine 126a uses a combination of techniques to both measure the progress of the user 104 within a particular period and determine if the user 104 has satisfied the requirements to transition to a successive period after a data exchange with the user device 110.

The program level engine 126b enables the program configuration module 126 to determine a level that indicates performance of the user 104 within a particular track. For instance, the program level engine 122 may extract track-specific data associated with each current track within the current content 114, and compare the track-specific data against a set of criteria to designate a level to the user 104 for each current track. In one example, where the data within a particular track includes quantitative data (e.g., heart rate measurements, breathing rate measurements), the program level engine 126b measures a performance level measure for each current track based on sensor data associated with user activity data. In another example, where the data within a particular track includes qualitative data (e.g., user survey information), the program level engine 126b estimates an intensity score based on a set of user attributes associating with well-being (e.g., depression, anxiety, psychological condition) and assigns a level based on where the intensity score falls within a range of scores associated with each level.

The rules engine 126c enables the program configuration module 126 to identify applicable rules that are associated with the program and determine whether one or more conditions for the applicable rules have been satisfied. For instance, the rules engine 126c may extract the data included in the current content 114 and initially select a subset of applicable rules from among the global rules 124c.

After selecting the applicable rules, the rules engine 126c then compares the extracted data against requirements for each of the applicable rules to determine if a trigger associated with the applicable rules or one or more conditions associated with the applicable rules have been satisfied. For example, such criteria can include a minimum measurement value for a particular user parameter as described throughout, or a presence of specific event within the current content 114 indicating that the user 104 associated with a milestone of the program (e.g., data indicating that the user 104 is able to walk in a rehabilitative physical therapy treatment program). In this example, a trigger may be used to enable the program configuration module 126 to transmit a set of instructions within the personalized content 116 for the mobile application 112 to adjust the display of content related to the program. Likewise, the satisfaction of one or more conditions can be used to determine transitions associated with the current data (e.g., upgrades to a new level within a track, determining that the user has advanced to a new period). In this regard, techniques used by rules engine 126c with respect to triggers and conditions associated with applicable rules enable the program configuration module 126 to produce variations of content to provided based on prior user activity on the mobile application 112.

Figure 2:
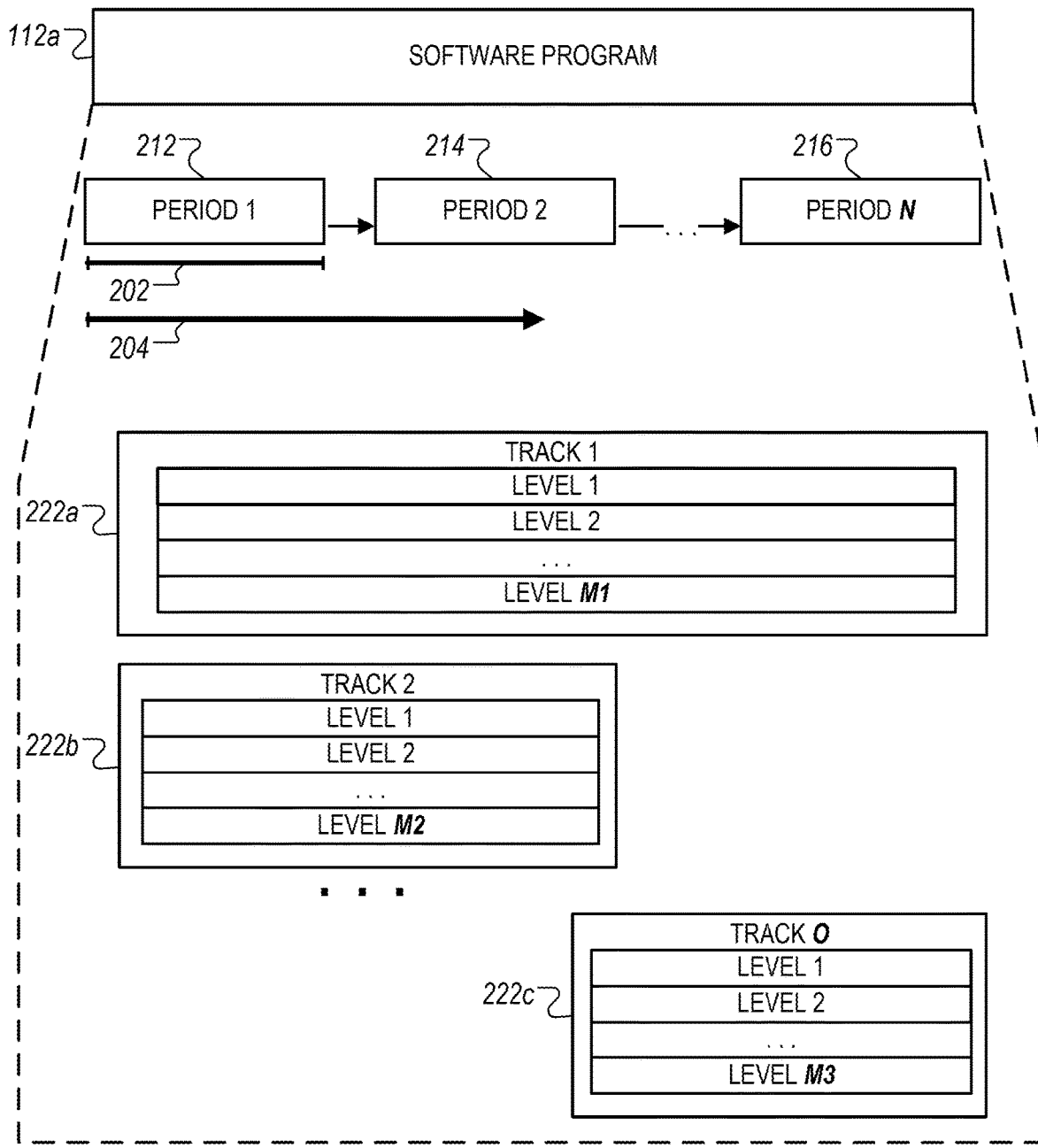
FIG. 2 is a diagram that illustrates an example of a multi-level content architecture.

FIG. 2 is a diagram that illustrates an example of a multi-level content architecture 200. In general, a program 202 includes a program sequence defined by a series of periods with defined time lengths including periods 212, 214, and 216. For example, the period 212 has a corresponding time length 202. As described previously with respect to FIG. 1A, each of the periods 212, 214, and 216 may have corresponding requirements indicative of a user's progress within the program 202. As an example, the periods 212, 214, and 216 can represent different stages or phases of a clinical treatment plan (e.g., diagnosis, disease control, restorative, and maintenance).

Although FIG. 2 depicts the program 112a as having multiple periods 212, 214, and 214, each with multiple tracks 222a, 222b, and 222c, in some implementations, the program 112a includes a single period with either a single track and/or multiple tracks. In addition, as depicted in FIG. 2, the different tracks within the program 112a can have different corresponding lengths within the program sequence specified by the arrangement of the periods.

As described herein, a progress measure 204 can be used to indicate a user's development through respective periods (e.g., periods 212, 214, and 216) and through the overall program 202. In some instances, the progress measure 204 can be computed based on comparing user activity data received on the mobile application 112 to requirements associated with each of the respective periods to determine if the user has satisfied the requirements to transition between sequential periods. For example, exercise measurements (e.g., heart rate, calories burned, blood pressure) indicating a user fitness level submitted on the mobile application 112 can be used to compared against a minimum fitness level for different periods of a physical therapy program to determine an appropriate time to transition the user between successive periods.

As depicted in FIG. 2, each period also includes a set of user-selectable tracks 222a, 222b, and 222c. Each of the tracks 222a, 222b, and 222c represent alternative content that can be provided for display on the mobile application 122 based the data included within the current content 116, and the program data stored on the database 122. For instance, as described previously with respect to FIG. 1A, the program configuration module 126 can processes user information (e.g., current tracks, current period) included within the current content 116 to identify rules associated with the current tracks, and compares the data included in the current content 116 against stored content 124 to determine whether a trigger associated with the identified rule has been satisfied, and/or if one or more conditions specified by the identified rule are also satisfied. More particular descriptions related to the comparison techniques used by the program configuration module 126 are described below with respect to FIG. 3.

Each track includes a set of levels that are used to indicate a user performance level measure representing a user's activities within a particular track. In some instances, the different levels can represent different difficulties associated with activities performed by the user during the track. For example, different levels within an exercise track that determines a user fitness level can represent exercise regimens of varying intensities (e.g., a relaxing walk, a mild jog, a sprint), or varying time lengths of activities (e.g., a five-minute warm-up walk, a half-mile jog, a half-marathon run). In other instances, the different levels can represent severities across a predetermined spectrum. For example, an anxiety track may include different levels that represent measured anxiety levels associated with the user based on the user's submitted responses to surveys presented on the program. In both of these examples, the levels can be used as indicators for a user's performance level within a particular track such that measurements of the user's current level over a period of time can be used to represent a user's progress within the track as the user progresses through the period that includes various tracks.

Figure 3:
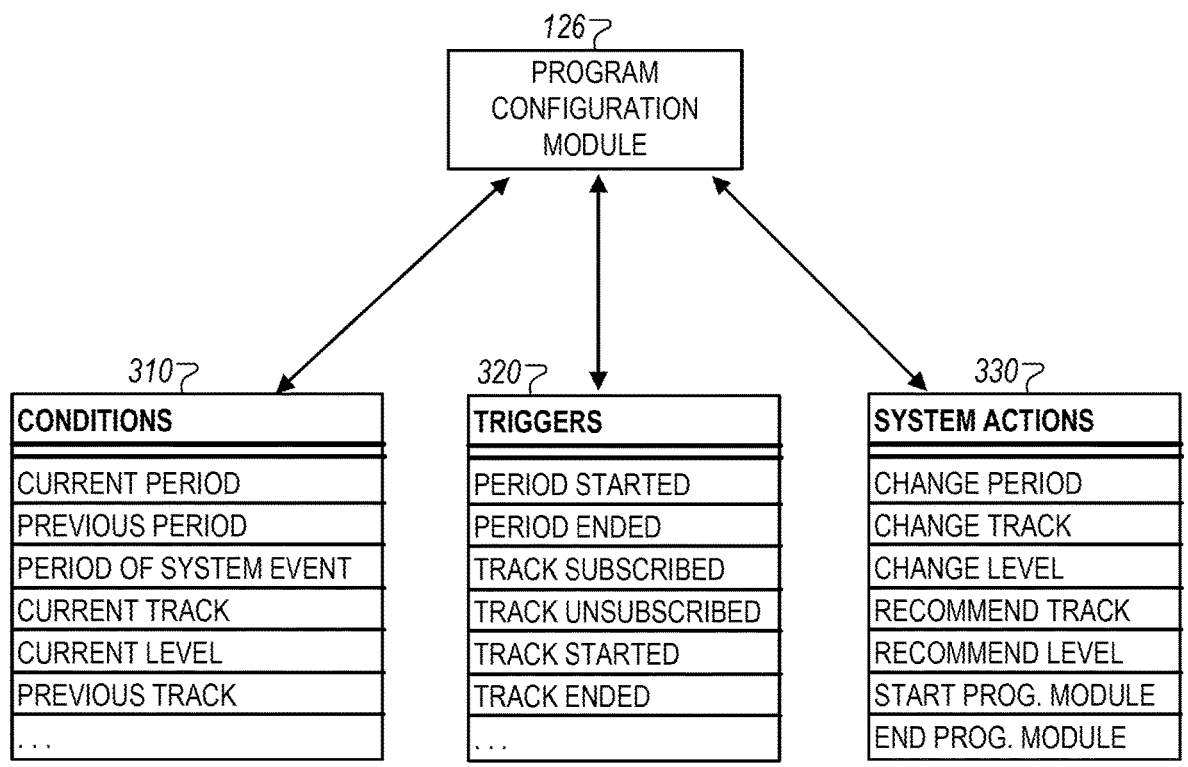
FIG. 3 is a diagram that illustrates examples of data that can be used to generate content adjustments.

FIG. 3 is a diagram that illustrates examples of different types of data that can be used to generate provide personalized content. The program configuration module 126 can use a set of conditions 310, triggers 320, and system actions 330 to both identify applicable rules, from among the global rules 124c, for the current content 114 of the program. As described previously, the current content 114 may specify a current period indicating the progress of the user 104 within the program, the currently available tracks within the current period, and the measured level for each of the current tracks associated with the user.

The applicable rules selected by the program configuration module 126 using a variety of selection techniques. In some instances, the rules within the global rules 124c can be predetermined to be associated with specific types of programs (e.g., preventative care programs vs. palliative care programs). In such instances, the program configuration module 126 may determine a program category associated with the program, and filter the global rules 124c based on the determined program category. In other instances, the rules within the global rules 124c can be selected based on other factors such as attributes of the data included within the current content 114 (e.g., qualitative vs. quantitative data), the particular tracks selected to participate in by the user, the arrangement of tracks within the current period, among other factors.

In some implementations, the applicable rules selected by the program configuration module 126 can be based on relationships between historical data for the user associated with the program (e.g., prior content accessed) and the data included within the current content 114. For example, a rule associated with a particular track may be selected if the comparison suggests that the user has repeatedly selected the particular track over multiple periods within the program sequence of the program. In another example, a transitional rule that describes actions to be performed as a result of a transition (e.g., between levels within a track, between periods within the program sequence) if the comparison suggests that either the level within the tracks have changed, the arrangement of the available tracks within a particular period has changed, or if the user has advanced or digressed to a different period than the last period.

The program configuration module 126 also uses data within the current content 114 to determine if triggers or conditions associated with the applicable rules have been satisfied. FIG. 3 illustrates of certain types of data that can be used to determine whether triggers or conditions have been satisfied. For example, if a rule includes a condition that specifies the user 104 to be in a particular period within the program sequence of the program, then the program configuration module 126 may compare the current period indicated by the current content 114 and determine whether the current period corresponds the particular period specified by the rule condition.

In other examples, the rule can include other conditions that associate specific system events and a particular period within a program sequence. For instance, a system event can include backend processes performed by the servers 120 and 130 (e.g., initiating a data transmission with the user device 110, storing the current content 114 within the database 122, generating the personalized content 116 to transmit to the user device 110). In these examples, if the current content 114 specifies a current period that satisfies the rule, the program configuration module 126 determines that the rule has been satisfied. For example, satisfaction of the rule can be used to coordinate the execution backend processes that adjust the selection of content to be provided on the mobile application 112, or adjust the comparison techniques between the current content 114 and the stored content 124.

The satisfaction of the rules selected by the program configuration module 126 can also be based on triggers. For instance, the program configuration module 126 may compare the data within the current content 114 against the historical data within the stored content 124b to determine changes that correspond to changes specified by triggers. In one example, if the current content 114 indicates that the user 104 has initiated a new period within the program sequence since the last data transmissions, the program configuration module 126 determines that a trigger for a rule that controls the display of notifications on the mobile application 112 is satisfied, and in response, transmits an instruction to display a notification on the mobile application 112 congratulating the user in beginning a new period. In other examples, the triggers associated with the selected rules can be associated when a user subscribes, unsubscribes, starts, or completes an available track within a period or when a user completes a track within the period.

FIG. 4 is a diagram that illustrates examples of rules that can be used by the program configuration module 126 to adjust content associated with a program. As depicted, rule list 410 includes four rules that are each associated with a "dog walking" track within a program focused on improving a user's physical fitness. Each period within this program corresponds to different stage of physical fitness, which may be monitored based on the frequency of activities performed by the user. Each track corresponds to a different physical activity (e.g., walking the dog, going for a jog, weight lifting), which can be used to monitor different aspects of physical fitness (e.g., endurance, stamina, strength, flexibility). Each track also includes a level indicating the intensity of the activity performed by the user.

The rules included in the list 410 can be used to perform certain system actions based on determining whether the data transmitted from the user device 110 satisfies one or more conditions or triggers associated with each rule. In some instances, the different rules can be used to perform alternate content delivery actions. For example, the triggers and conditions for program rules 1 and 2 can be used to perform different system actions (e.g., assessment 1 or assessment 2) and deliver different categories of content (e.g., video 1 and email 1, or video 2 and email 2). In this example, the different conditions between the rules can be used to perform the specific content delivery action based on the specific level within the current track (e.g., moderate vs. vigorous). In other instances, the different rules can be used to provide different categories of content to the mobile application 112. For example, in response to satisfying either program rule 3 or program rule 4, a content item from either category A or category B can be provided for display on the mobile application. In this example, satisfaction of the condition is based on the user's progress within the track (e.g. no change in level, increase in the level, or decrease in the level).

Although FIG. 4 illustrates different rules that are used to provide alternate content delivery actions, in some implementations, different sets of discrete rules can be used in combination to customize the content provided to the mobile application 112. For example, the different sets of rules can be based on the user's progress within the program (e.g., using a set of rules directed to the period), a user's performance with a single track (e.g., using a set of rules directed to the levels of the single track), a user's performance within multiple tracks within the period (e.g., using a set of rules directed to comparing user's enrollment and subscription into different tracks), and time-based changes in the user's activities within the program sequence (e.g., using sets of rules directed to detecting changes in period, track, and level). In such implementations, the triggers and conditions associated with the different rules can be used to identify certain changes that are likely to impact a user's experience within the program.

Figure 5A:
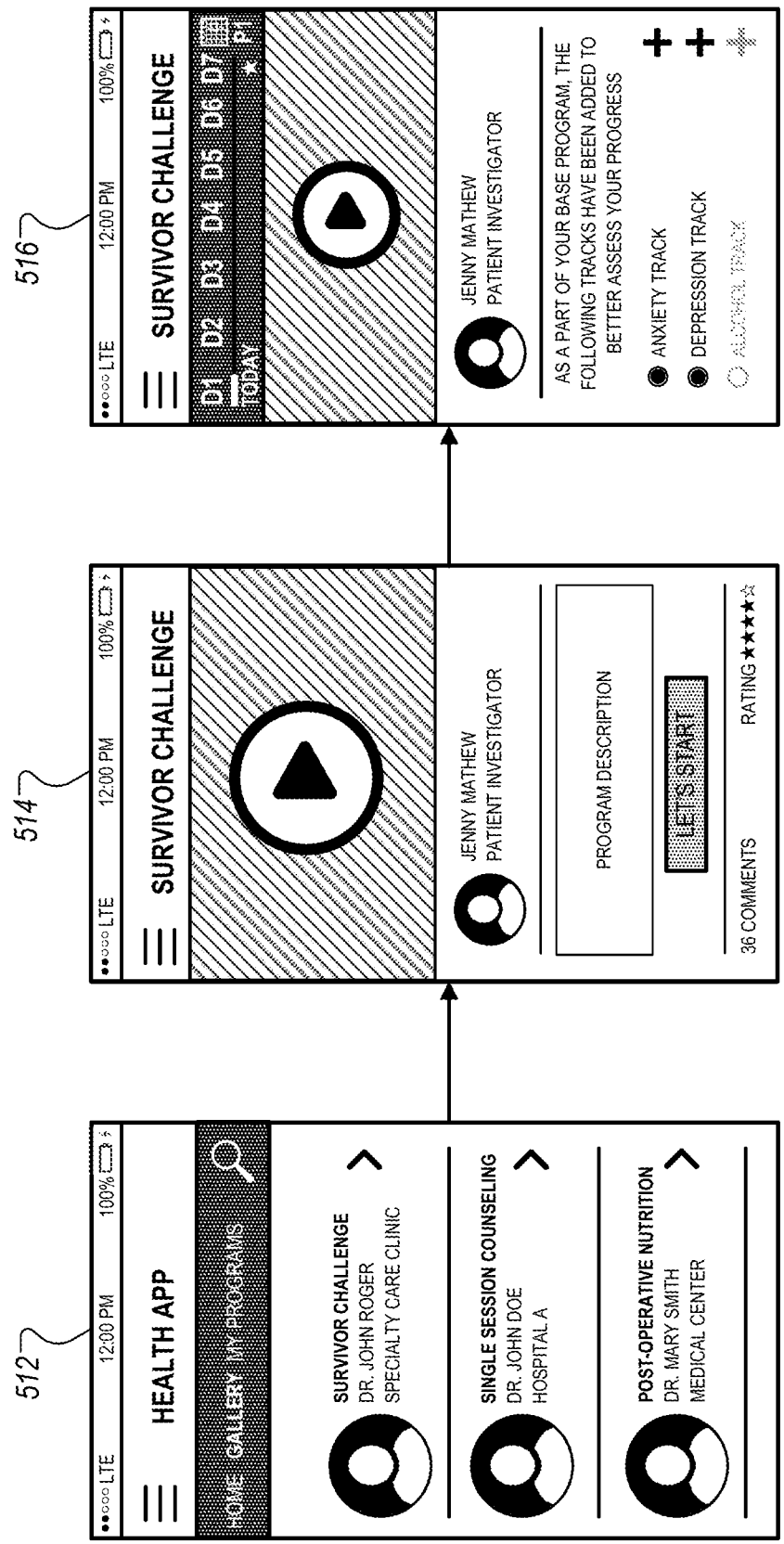
FIGS. 5A-5C are diagrams that illustrate examples of user interfaces for providing personalized content.
Figure 5B:
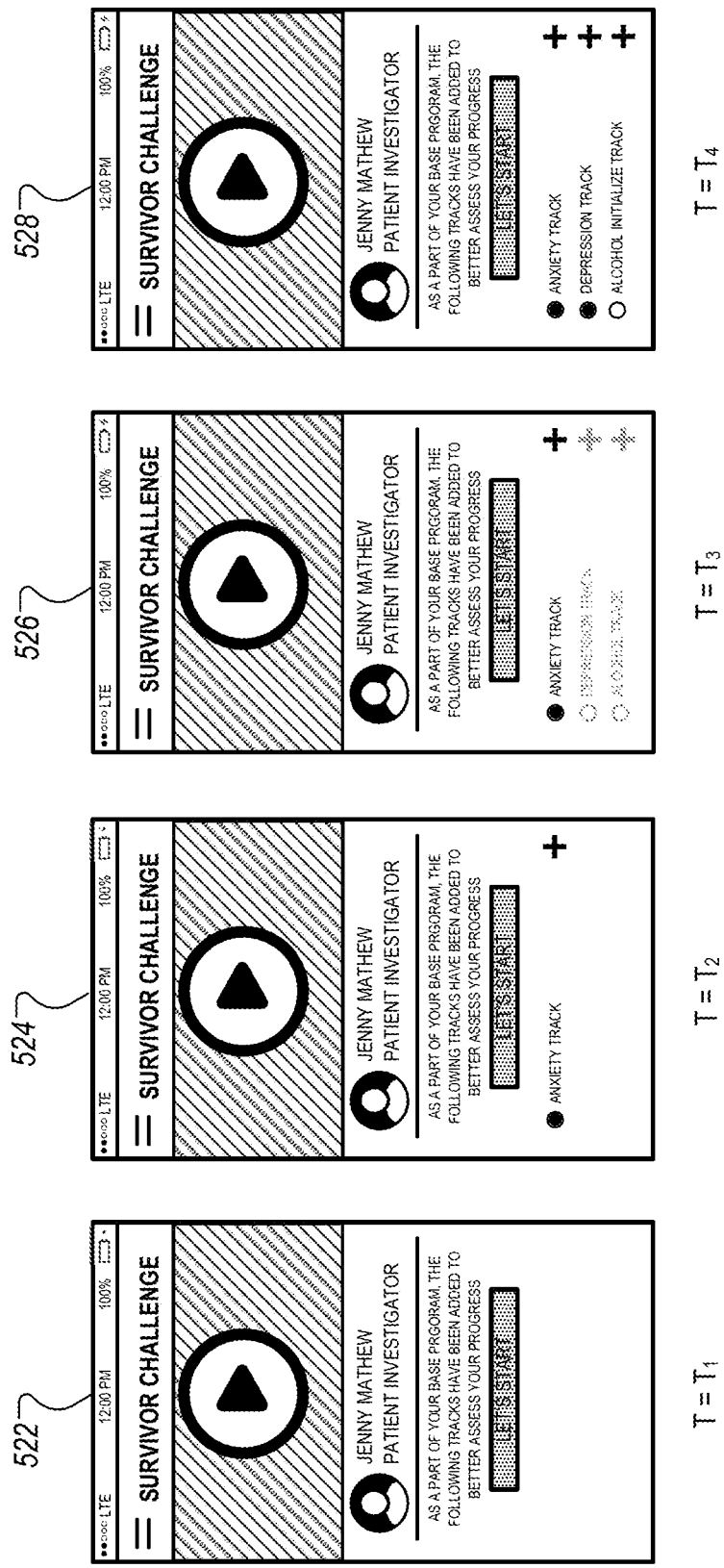
Figure 5C:
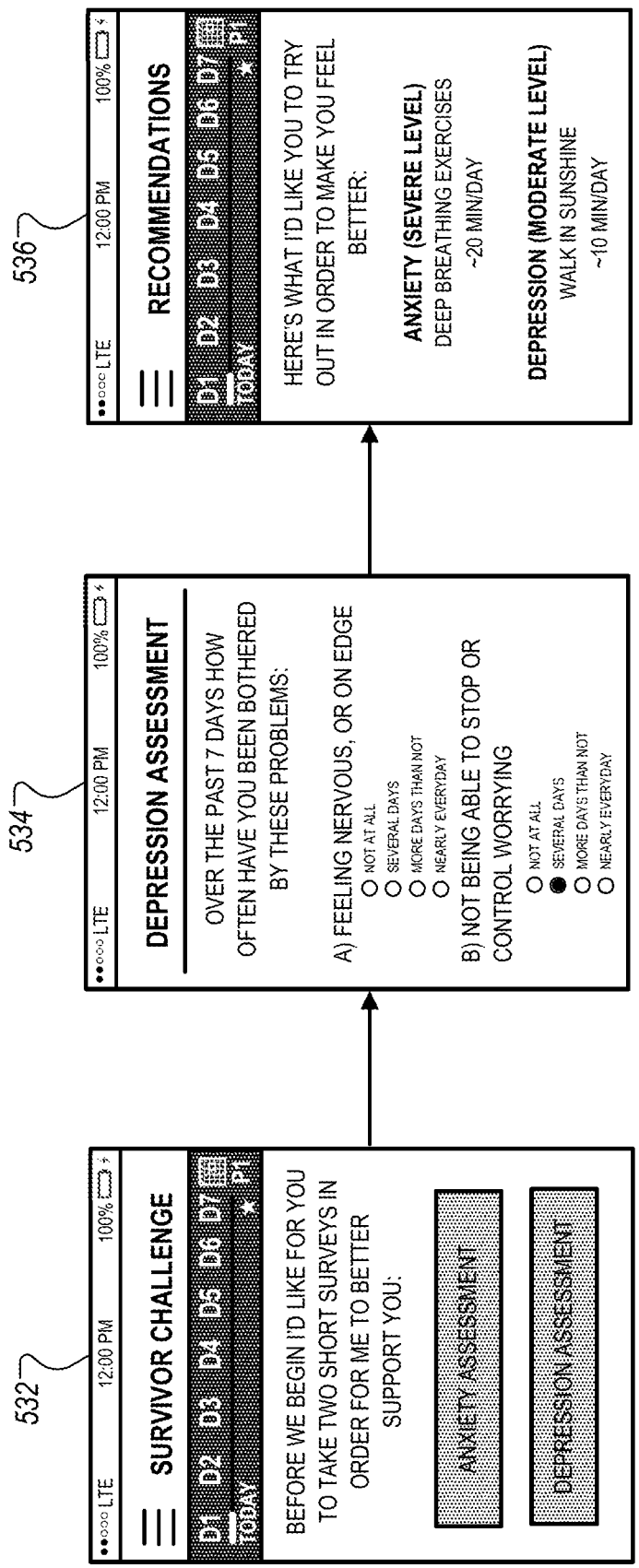

FIGS. 5A-5C are diagrams that illustrate examples of user interfaces for providing personalized content. FIG. 5A illustrates an example of user interfaces that enable to enroll into a program. FIG. 5B illustrates various user interfaces that represent different instances of the mobile application 112 based on the content transmitted from the server 120. FIG. 5C illustrates interfaces that are used to collect information from a user, assess the collected information, and provide recommendations for tracks and levels based on the assessments.

Referring to FIG. 5A, the user 104 may initially be presented with a list of different programs on a gallery interface 512. In the examples illustrated in FIG. 5A, the programs include "Survivor Challenge," "Single Session Counseling," and "Post-Operative Nutrition." The interface 512 additionally includes information associated with each program such as the healthcare provider and the related institution. Such information is provided to assist a user to select an appropriate program that is relevant to the user.

In some implementations, the list of programs provided on the interface 512 may be selected for the user 104 based on user-specific information. For example, the user 104 may be requested to complete an initial registration survey when the user 104 installs the mobile application 112 on the user device 110. The survey can include request for a user's primary healthcare provider, health insurance company, medical history, and other types of user-identifying information. The information submitted on the survey can then be used by the server 120 to determine the programs that are determined to be relevant to the user 104.

In some implementations, the list of available programs provided on the interface 512 can be periodically updated by the server 120 based on the user data submitted on the mobile application 112. For instance, if a user enrolls into a particular program focused on post-operative recovery, then the server 120 may determine other programs that are associated to the enrolled program (e.g., similar programs enrolled into by other patients who have enrolled into post-operative recovery programs, other programs that are complementary to post-operative recovery programs). The other programs can then be provided on the interface 512 as the user 104 progresses through the post-operative recovery program.

In the example in FIG. 5A, the user 104 selects the "Survivor Challenge" program on the interface 512 and is then directed to the interface 514. The interface 514 is a program-specific interface that provides program information to the user 104. For example, the interface 514 can provide information for a healthcare provider such as a patient investigator, a program description providing an overview of the program sequence, and/or media content associated with the program. The interface 514 can also display user-submitted feedback such as reviews and ratings from other users that have previously participated in the program.

Once the user 104 enrolls into program on the interface 514, the user 104 is then directed to the interface 516. The interface 516 provides program-related information such as the period information (indicated as P1 in the interface 516), track information (e.g., available tracks and unavailable tracks) and options for the user to subscribe to available tracks. The interface 516 may also provide media content that overviews the entire program and provides the user 104 with a comprehensive view of the program sequence of the program.

In some implementations, the initial tracks available for access to the user may be predetermined based on a set of baseline tracks that are available to all users that initially enroll into the program. In such implementations, the user can be provided with access to the baseline tracks (e.g., Anxiety Track and Depression Track in the FIG.), but not provided with access to additional tracks (e.g., Alcohol Track) until the user has either completed or achieved a certain performance level with the baseline tracks. For example, the Alcohol Initialize Track may become available to the user 104 based on either the user completing one or both of the Anxiety Track and Depression Track, the user 104 achieving a minimum performance level within each of these tracks to satisfy the criteria for the Alcohol Track. In each of these examples, access to the additional tracks may be governed with the use of rules to determine whether the user 104 has satisfied a set of conditions or triggers as described previously with respect to FIGS. 3-4.

Referring now to FIG. 5B, the interface 516 can be adjusted at different time points to alternate configurations specified by different rules as described previously with respect to FIG. 4. The configurations of the interfaces 522, 524, 526, and 528 can be adjusted based on a user's progress through the program. For instance, the interface 522 represents an example of an interface when the user 104 initially enrolls into the program. In this example, relatively simple configuration of the interface provides the user 104 with access to a base track without any additional tracks. This interface can be used to improve user experience when the user 104 has limited experience with the program to prevent confusion and/or ease the user 104 into the program.

The interface 524 illustrates an example of an interface where the user 104 may be provided with access to an optional "Anxiety Track" in addition to the baseline track for the program. In some implementations, the optional track is automatically provided based on determining that it is commonly associated with the program. For instance, the optional track may be provided because historical data associated with the program indicates that other users who have previously participated in the program have enrolled into the track from a list of optional tracks. In other implementations, the optional track may be provided based specifically on user-specific information associated with the user 104. For instance, the user may complete an initial survey when enrolling into the program, which can then be used to determine a set of baseline attributes used to determine optional tracks of interest. In such instances, the decision to provide an optional track can be used to customize the program for the user 104.

The interface 526 illustrates an example of an interface that provides optional tracks that are not presently accessible (e.g., Depression Track and Alcohol Track). In this example, access to the optional tracks may be controlled using the rule satisfaction techniques described throughout this disclosure. For example, access to the optional tracks may be restricted to provide the user 104 with an incentive to increase participation in the presently available tracks (e.g., the baseline track and the Anxiety Track) until the progress or performance level of the user 104 exceeds a minimum value specified by one or more associated rules. In one example, access to the restricted tracks may be provided after the user progresses to a certain period within the program sequence of the program. In this example, the user 104 may progress through the period based on the passage of time (e.g., a seven-day period), or based on the performance level measure of the user 104 within each of the available tracks (e.g., achieving higher levels within the baseline track and the Anxiety Track). In another example, access to the restricted tracks may be manually provided by the administrator 102 after reviewing user data (e.g., survey information, performance on tracks) submitted on the mobile application 112. In this example, the interface 526 enables the administrator 102 to use the program configuration module 126 dynamically provide content that is directed to improving the experience and progress of the user 104 through the program.

The interface 528 illustrates an example of an interface that provides the user 104 with the ability to select from a list of optional tracks. In this example, the tracks included in list of optional tracks are initially selected to be provided on the interface 528 based on a variety of factors described above with respect to the interface 522. This enables the user 104 to select a customized experience within the program based on the selections from the list of optional tracks. In addition, as described throughout, the selections of the optional tracks can then be used to adjust the techniques used by the program configuration module 126 to both identify the applicable rules and determine whether the conditions and rules of the applicable rules have been satisfied after receiving data transmissions from the user device 110.

Although the interfaces 522, 524, 526, and 528 are described as alternative interfaces, in some instances, the interfaces 522, 524, 526, and 528 can be different instances of the mobile application 112 over a period of time. In such instances, the interface 522 is presented to the user at time point t1, and the interfaces 524, 526, and 528 are subsequently presented to the user at time points t2, t3, and t4, respectively. The transition between time point t1 and t4 reflects the addition of supplemental content and various access settings on the program as the user progress through different periods of the program sequence of the program.

Referring now to FIG. 5C, interfaces 532, 534, and 536 can be used to collect information from the user 104, assess the collected information, and provide recommendations for tracks and levels based on the assessments. For instance, the interface 532 may present the user 104 with the option to participate in assessment surveys related to subscribed tracks within the program.

The user can select an assessment and then be directed to the interface 534 to answer questions that are relevant to the selected track. For instance, the interface 534 requests the user to provide answers to questions related to the selected track. In the example, the questions are directed to determine a depression level of the user based on questions related to the user's feelings of nervousness and lack of control.

After user 104 completes the assessment survey on the interface 534, the collected data may be analyzed by either the user device 110 or the server 120. For instance, the user responses included within the collected data may be analyzed against previously submitted responses by the user, prior responses submitted by other users who have completed similar survey assessments, or other types of statistical data models. The server 120 can then determine a level associated with the user responses and then provide the level determinations on the interface 136.

The interface 536 can also provide recommendations to the user 104 based on the determined levels for each of the tracks. In the examples illustrated, the interface 536 provides a recommendation to perform deep breathing exercises in response to determining a severe anxiety level, and a recommendation to walk in sunlight in response to determining a moderate depression level. In this regard, the user-submitted information can be used to automatically provide the user 104 with feedback on improving his/her performance within the available tracks within the program.

In some implementations, the level determinations can be used to further adjust the content displayed to the user 104 on the program. For example, as described throughout this disclosure, in response to determining the track levels and generating user recommendations, the program configuration module 126 may also identify additional tracks that are associated with the recommendations and provide the additional tracks for display on the program. In other examples, the program configuration module 126 may perform other system actions such as providing additional notifications and/or messages to the user to improve motivation of the user 104, adjusting the layout of the content within the program, or enable the user to subscribe into other tracks that are more suitable to the recommendations than the currently available tracks.

Figure 6:
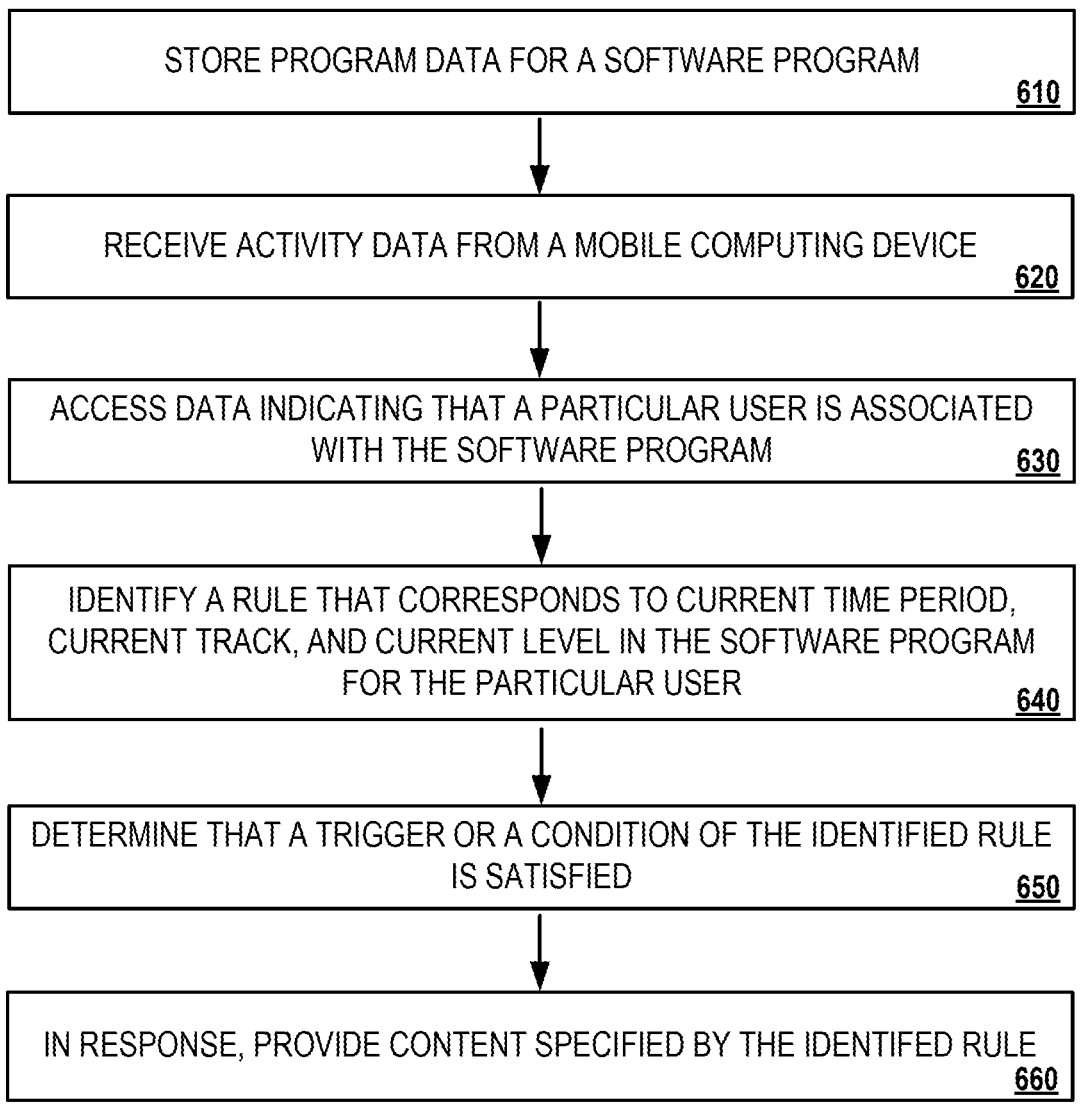
FIG. 6 is a diagram of an example of a process for providing personalized content based on an identified rule.

FIG. 6 is a diagram of an example of a process 600 for providing personalized content based on an identified rule. Briefly, the process 600 can include storing program data for a program (610), receiving activity data from a mobile computing device (620), accessing data indicating that a particular user is associated with the program (630), identifying a rule that corresponds to a current time, current track, and current level in the program for the particular user (640), determining that a trigger or a condition of the identified rule is satisfied (650), and in response, providing content specified by the identified rule (660).

In more detail, the process 600 can include storing program data for a program (610). For instance, the server 120 stores program data for a program 112a such as the stored user data 124a and the stored content 124b. The stored program data provides interactive content over a program sequence that includes a series of multiple time periods such as periods 212, 214, and 216. As described previously with respect to FIG. 2, the program 112a includes multiple selectable tracks 222a, 222b, and 222c, and multiple levels within each track. The program data also indicates global rules 124c for the program that vary the interactive content provided to different users according to at least the respective tracks, levels, and time periods of the different users in the program.

The process 600 can include receiving activity data from a mobile computing device (620). For instance, the server 120 can receive activity data from the user device 110 that indicates interaction of the user 104 during a particular period of the multiple time periods 212, 214, and 216 of the program 112a. As described previously with respect to FIG. 1A, the data can include user inputs provided by the user on the mobile application 112, selections of particular tracks that the user 104 decides to subscribe to, or responses to assessment surveys provided on the mobile application 112.

The process 600 can include accessing data indicating that a particular user is associated with the program (630). For instance, the server 120 can access the current content 114 from the mobile application 112 that indicates that the user 104 is associated with the program on the user device 110. The current content 114 can include a current time period, a current track, and a current level for the user 104 in the program. As described previously with respect to FIG. 1A, the server 120 can periodically access the current content 114 over intervals of time to determine the progress of the user 104 through the program, and other changes in the current content over time.

The process 600 can include identifying a rule that corresponds to a current time, current track, and current level in the program for the particular user (640). For instance, the server 120 can identify an applicable rule from among the global rules 124c that corresponds to the current time period, the current track, and the current level in the program for the user 104. As described previously with respect to FIG. 3, the applicable rule can be selected based on comparing the current content 114 to the program data stored on the database 122.

The process 600 can include determining that a trigger or a condition of the identified rule is satisfied (650). For instance, the server 120 can determine that the trigger and the condition of the identified rule is satisfied based on determining that portions of the current content 122 correspond to the requirements specified by the identified rule.

The process 600 can include providing content specified by the identified rule in response to determining that the trigger or the condition of the identified rule is satisfied (660). For instance, in response to determining that the trigger or the condition of the identified rule is satisfied, the server 120 can transmit the personalized content 116 to user device 110 for display on the mobile application 112. As described previously with respect to FIG. 1A, the personalized content 116 can include additional content (e.g., new tracks) that the user 104 did not previously have access to, instructions to adjust the display of content (e.g., removing access to tracks completed by the user 104), notifications and/or messages to be displayed on the interface of the mobile application 112 (e.g., a user survey provided in response to user performance within a certain track), among other types of content.

Figure 7:
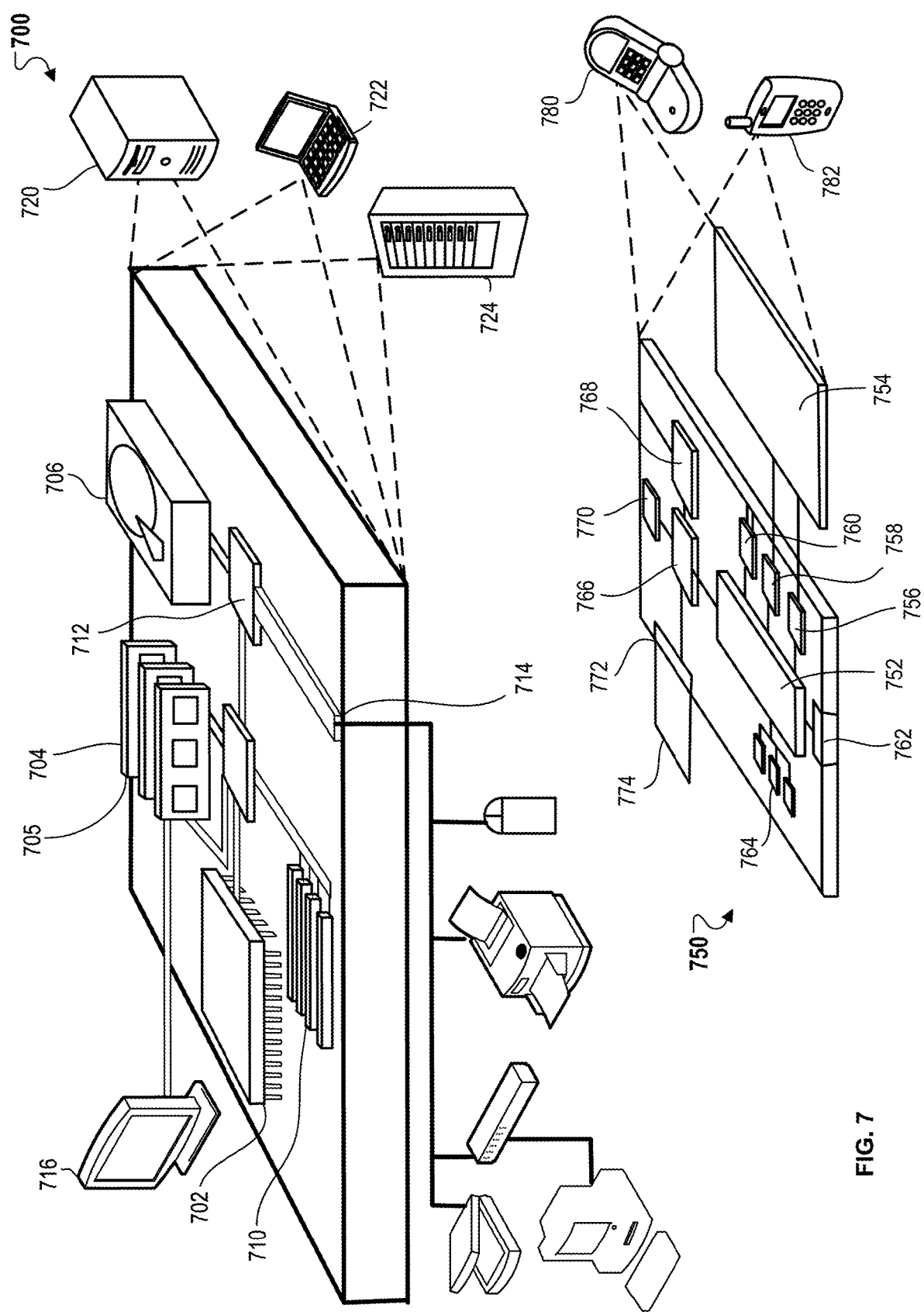
FIG. 7 is a block diagram of computing devices on which the processes described herein, or potions thereof, can be implemented.

FIG. 7 is a block diagram of computing devices 700, 750 that can be used to implement the systems and methods described in this document, as either a client or as a server or plurality of servers. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smartphones, and other similar computing devices. Additionally, computing device 700 or 750 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses can be used, as appropriate, along with multiple memories and types of memory. Also, multiple computing devices 700 can be connected, with each device providing portions of the necessary operations, e.g., as a server bank, a group of blade servers, or a multi-processor system.

The memory 704 stores information within the computing device 700. In one implementation, the memory 704 is a volatile memory unit or units. In another implementation, the memory 704 is a non-volatile memory unit or units. The memory 704 can also be another form of computer-readable medium, such as a magnetic or optical disk.

The storage device 706 is capable of providing mass storage for the computing device 700. In one implementation, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 704, the storage device 706, or memory on processor 702.

The high speed controller 708 manages bandwidth-intensive operations for the computing device 700, while the low speed controller 712 manages lower bandwidth intensive operations. Such allocation of functions is exemplary only. In one implementation, the high-speed controller 708 is coupled to memory 704, display 716, e.g., through a graphics processor or accelerator, and to high-speed expansion ports 710, which can accept various expansion cards (not shown). In the implementation, low-speed controller 712 is coupled to storage device 706 and low-speed expansion port 714. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 700 can be implemented in a number of different forms, as shown in the figure. For example, it can be implemented as a standard server 720, or multiple times in a group of such servers. It can also be implemented as part of a rack server system 724. In addition, it can be implemented in a personal computer such as a laptop computer 722. Alternatively, components from computing device 700 can be combined with other components in a mobile device (not shown), such as device 750. Each of such devices can contain one or more of computing device 700, 750, and an entire system can be made up of multiple computing devices 700, 750 communicating with each other.

The computing device 700 can be implemented in a number of different forms, as shown in the figure. For example, it can be implemented as a standard server 720, or multiple times in a group of such servers. It can also be implemented as part of a rack server system 724. In addition, it can be implemented in a personal computer such as a laptop computer 722. Alternatively, components from computing device 700 can be combined with other components in a mobile device (not shown), such as device 750. Each of such devices can contain one or more of computing device 700, 750, and an entire system can be made up of multiple computing devices 700, 750 communicating with each other.

Computing device 750 includes a processor 752, memory 764, and an input/output device such as a display 754, a communication interface 766, and a transceiver 768, among other components. The device 750 can also be provided with a storage device, such as a microdrive or other device, to provide additional storage. Each of the components 750, 752, 764, 754, 766, and 768, are interconnected using various buses, and several of the components can be mounted on a common motherboard or in other manners as appropriate.

The processor 752 can execute instructions within the computing device 750, including instructions stored in the memory 764. The processor can be implemented as a chipset of chips that include separate and multiple analog and digital processors. Additionally, the processor can be implemented using any of a number of architectures. For example, the processor 710 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 750, such as control of user interfaces, applications run by device 750, and wireless communication by device 750.

Processor 752 can communicate with a user through control interface 758 and display interface 656 coupled to a display 754. The display 754 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 754 to present graphical and other information to a user. The control interface 758 can receive commands from a user and convert them for submission to the processor 752. In addition, an external interface 762 can be provide in communication with processor 752, so as to enable near area communication of device 750 with other devices. External interface 762 can provide, for example, for wired communication in some implementations, or for wireless communication in other implementations, and multiple interfaces can also be used.

The memory 764 stores information within the computing device 750. The memory 764 can be implemented as one or more of a computer-readable medium or media, a volatile memory unit or units, or a non-volatile memory unit or units. Expansion memory 764 can also be provided and connected to device 750 through expansion interface 762, which can include, for example, a SIMM (Single In Line Memory Module) card interface. Such expansion memory 764 can provide extra storage space for device 750, or can also store applications or other information for device 750. Specifically, expansion memory 764 can include instructions to carry out or supplement the processes described above, and can include secure information also. Thus, for example, expansion memory 764 can be provide as a security module for device 750, and can be programmed with instructions that permit secure use of device 750. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 764, or memory on processor 752 that can be received, for example, over transceiver 768 or external interface 762.

Device 750 can communicate wirelessly through communication interface 766, which can include digital signal processing circuitry where necessary. Communication interface 766 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 768. In addition, short-range communication can occur, such as using a Bluetooth, Wi-Fi, or other such transceiver (not shown). In addition, GPS (Global Positioning System) receiver module 660 can provide additional navigation- and location-related wireless data to device 750, which can be used as appropriate by applications running on device 750.

Device 750 can also communicate audibly using audio codec 660, which can receive spoken information from a user and convert it to usable digital information. Audio codec 660 can likewise generate audible sound for a user, such as through a speaker, e.g., in a handset of device 750. Such sound can include sound from voice telephone calls, can include recorded sound, e.g., voice messages, music files, etc. and can also include sound generated by applications operating on device 750.

The computing device 750 can be implemented in a number of different forms, as shown in the figure. For example, it can be implemented as a cellular telephone 480. It can also be implemented as part of a smartphone 682, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method performed by one or more computers, the method comprising:
   providing, by the one or more computers, data for a program comprising a sequence of multiple different segments that each have a corresponding (i) set of content and (ii) set of rules that indicate triggers or conditions for presenting interactions using the content from the set of content for the segment, each of the segments being configured to provide interactions from a respective set of interactions to monitor or improve health of a user, wherein the interactions are provided through a mobile device of the user;
   monitoring, by the one or more computers, (i) progress of the user through the sequence of multiple different segments and (ii) actions performed by the user during a current segment in the sequence of multiple different segments;
   generating, by the one or more computers, a performance measure for the user for the current segment based on (i) health data provided during the current segment in one or more survey responses provided by the user through a user interface of the mobile device and (ii) monitored actions, performed by the user during the current segment, that are different from the user providing the survey responses;
   determining, by the one or more computers, that the performance measure satisfies a requirement for the current segment;
   based on determining that the performance measure satisfies the requirement for the current segment, updating, by the one or more computers, a progress measure for the progress of the user to indicate that the user has progressed from the current segment to a next segment within the sequence; and
   based on updating the progress measure, providing, by the one or more computers, data that causes the mobile device to enable a set of interactions for the next segment of the program to be selectively provided to the user through the mobile device based on the triggers or conditions of the rules in the set of rules corresponding to the next segment.

2. The method of claim 1, wherein determining that the performance measure satisfies the requirement for the current segment comprises determining that the performance measure satisfies a performance measure threshold for the current segment.

3. The method of claim 1, wherein providing data that causes the user device to enable the set of interactions provided by the next segment of the program comprises selecting a set of content with which interactions are to be provided to the user by the mobile device in the next segment of the program.

4. The method of claim 1, wherein the performance measure is generated based on an amount of time spent by the user in the current segment.

5. The method of claim 1, wherein the progress of the user through the sequence of multiple different segments is based at least in part on physiological data for the user.

6. The method of claim 1, further comprising:
determining, by the one or more computers, that the monitored progress of the user through the sequence of multiple different segments satisfies a progress level threshold of the program; and
providing, by the one or more computers, one or more additional interactions with the user during the current segment based on determining that the monitored progress of the user through the sequence of multiple different segments satisfies the progress level threshold of the program.

7. The method of claim 1, wherein each segment included in the sequence of multiple different segments is a different phase of a clinical treatment plan for the user.

8. A system comprising:
one or more computers; and
one or more storage devices storing instructions that, when executed by the one or more computers, cause the one or more computers to perform operations comprising:
providing, by the one or more computers, data for a program comprising a sequence of multiple different segments that each have a corresponding (i) set of content and (ii) set of rules that indicate triggers or conditions for presenting interactions using the content from the set of content for the segment, each of the segments being configured to provide interactions from a respective set of interactions to monitor or improve health of a user, wherein the interactions are provided through a mobile device of the user;
monitoring, by the one or more computers, (i) progress of the user through the sequence of multiple different segments and (ii) actions performed by the user during a current segment in the sequence of multiple different segments;
generating, by the one or more computers, a performance measure for the user for the current segment based on (i) health data provided during the current segment in one or more survey responses provided by the user through a user interface of the mobile device and (ii) monitored actions, performed by the user during the current segment, that are different from the user providing the survey responses;
determining, by the one or more computers, that the performance measure satisfies a requirement for the current segment;
based on determining that the performance measure satisfies the requirement for the current segment, updating, by the one or more computers, a progress measure for the progress of the user to indicate that the user has progressed from the current segment to a next segment within the sequence; and
based on updating the progress measure, providing, by the one or more computers, data that causes the mobile device to enable a set of interactions for the next segment of the program to be selectively provided to the user through the mobile device based on the triggers or conditions of the rules in the set of rules corresponding to the next segment.

9. The system of claim 8, wherein determining that the performance measure satisfies the requirement for the current segment comprises determining that the performance measure satisfies a performance measure threshold for the current segment.

10. The system of claim 8, wherein the performance measure is generated based on an amount of time spent by the user in the current segment.

11. The system of claim 8, wherein the progress of the user through the sequence of multiple different segments is based at least in part on physiological data for the user.

12. The system of claim 8, wherein each segment included in the sequence of multiple different segments is a different phase of a clinical treatment plan for the user.

13. At least one non-transitory computer-readable storage device encoded with computer program instructions that, when executed by one or more computers, cause the one or more computers to perform operations comprising:
providing, by the one or more computers, data for a program comprising a sequence of multiple different segments that each have a corresponding (i) set of content and (ii) set of rules that indicate triggers or conditions for presenting interactions using the content from the set of content for the segment, each of the segments being configured to provide interactions from a respective set of interactions to monitor or improve health of a user, wherein the interactions are provided through a mobile device of the user;
monitoring, by the one or more computers, (i) progress of the user through the sequence of multiple different segments and (ii) actions performed by the user during a current segment in the sequence of multiple different segments;
generating, by the one or more computers, a performance measure for the user for the current segment based on (i) health data provided during the current segment in one or more survey responses provided by the user through a user interface of the mobile device and (ii) monitored actions, performed by the user during the current segment, that are different from the user providing the survey responses;
determining, by the one or more computers, that the performance measure satisfies a requirement for the current segment;
based on determining that the performance measure satisfies the requirement for the current segment, updating, by the one or more computers, a progress measure for the progress of the user to indicate that the user has progressed from the current segment to a next segment within the sequence; and
based on updating the progress measure, providing, by the one or more computers, data that causes the mobile device to enable a set of interactions for the next segment of the program to be selectively provided to the user through the mobile device based on the triggers or conditions of the rules in the set of rules corresponding to the next segment.

14. The at least one non-transitory computer-readable storage device of claim 13, wherein determining that the performance measure satisfies the requirement for the current segment comprises determining that the performance measure satisfies a performance measure threshold for the current segment.

15. The at least one non-transitory computer-readable storage device of claim 13, wherein the progress of the user through the sequence of multiple different segments is based at least in part on physiological data for the user.

16. The at least one non-transitory computer-readable storage device of claim 13, wherein the operations further comprise:
- determining, by the one or more computers, that the monitored progress of the user through the sequence of multiple different segments satisfies a progress level threshold of the program; and
- providing, by the one or more computers, one or more additional interactions with the user during the current segment based on determining that the monitored progress of the user through the sequence of multiple different segments satisfies the progress level threshold of the program.

17. The method of claim 1, wherein the monitored actions that are different from the user providing the survey responses comprise monitored actions other than providing input to user interfaces of the mobile device.

18. The method of claim 1, wherein the monitored actions that are different from the user providing the survey responses comprise physical activity of the user that is sensed by the mobile device or another device.

19. The method of claim 1, wherein the monitored actions that are different from the user providing the survey responses comprise at least one action of the user in response to a notification that is caused by the program and is provided by the mobile device.

20. The method of claim 1, wherein the progress measure is based on results of one or more physiological measurements for the user that are performed during the current segment.

* * * * *